US009259408B2

(12) United States Patent
Domingo Pedrol et al.

(10) Patent No.: US 9,259,408 B2
(45) Date of Patent: *Feb. 16, 2016

(54) USE OF DHA, EPA OR DHA-DERIVED EPA FOR TREATING A PATHOLOGY ASSOCIATED WITH CELLULAR OXIDATIVE DAMAGE

(71) Applicants: Joan Carles Domingo Pedrol, Barcelona (ES); Jose Antonio Villegas Garcia, Murcia (ES)

(72) Inventors: Joan Carles Domingo Pedrol, Barcelona (ES); Jose Antonio Villegas Garcia, Murcia (ES)

(73) Assignee: Brudy Technology S.L., Barcelona (ES)

(*) Notice: Subject to any disclaimer, the term of this patent is extended or adjusted under 35 U.S.C. 154(b) by 0 days.

This patent is subject to a terminal disclaimer.

(21) Appl. No.: 13/803,038

(22) Filed: Mar. 14, 2013

(65) Prior Publication Data

US 2013/0274337 A1  Oct. 17, 2013

Related U.S. Application Data

(62) Division of application No. 12/158,205, filed as application No. PCT/EP2006/070016 on Dec. 20, 2006.

(30) Foreign Application Priority Data

Dec. 21, 2005 (ES) .................................. 200503202
Sep. 25, 2006 (ES) .................................. 200602417
Sep. 25, 2006 (ES) .................................. 200602418
Dec. 20, 2006 (ES) .................................. 200603231

(51) Int. Cl.
*A01N 37/06* (2006.01)
*A61K 31/22* (2006.01)
*A01N 37/02* (2006.01)
*A61K 31/225* (2006.01)
*A01N 37/00* (2006.01)
*A61K 31/20* (2006.01)
*A61K 31/202* (2006.01)
*A23L 1/30* (2006.01)
*A61K 47/12* (2006.01)

(52) U.S. Cl.
CPC .............. *A61K 31/202* (2013.01); *A23L 1/3008* (2013.01); *A61K 47/12* (2013.01)

(58) Field of Classification Search
USPC ........................................................ 514/549
See application file for complete search history.

(56) References Cited

U.S. PATENT DOCUMENTS 5,434,183 A * 7/1995 Larsson-Backstrom ...... 514/549
6,245,811 B1 6/2001 Horrobin et al.
6,313,167 B1 11/2001 Nakajima et al.
6,509,178 B1 1/2003 Tanaka et al.
6,582,941 B1 6/2003 Yokochi et al.
2004/0122093 A1 6/2004 Gandhi
2004/0209953 A1 10/2004 Wai Lee
2005/0027004 A1 2/2005 Kyle et al.
2005/0075398 A1 4/2005 Bazan et al.
2005/0106272 A1 5/2005 Lang et al.
2005/0136130 A1 6/2005 Lang
2005/0163873 A1 7/2005 Ritch

FOREIGN PATENT DOCUMENTS

| EP | 0342795 A2 | 11/1989 |
|---|---|---|
| EP | 1247523 A | 10/2002 |
| FR | 2 882 894 | 11/2005 |
| GB | 2218984 A | 11/1989 |
| WO | WO 90/04391 | 5/1990 |
| WO | WO 98/28978 A1 | 7/1998 |
| WO | WO 00/44361 | 8/2000 |
| WO | WO 03/068216 A1 | 8/2003 |
| WO | WO 2004/112776 A2 | 12/2004 |
| WO | WO 2005/013908 A2 | 2/2005 |
| WO | WO 2005/070411 A1 | 8/2005 |
| WO | WO 2006/077495 A1 | 7/2006 |
| WO | WO 2006/120120 A1 | 11/2006 |
| WO | WO 2007/071733 A3 | 6/2007 |

OTHER PUBLICATIONS

Bazan ("Neuroprotectin D1 (NPD1): A DHA-Derived Mediator that Protects Brain and Retina Against Cell Injury-Induced Oxidative Stress." Brain Pathology 15.2 (2005): 159-166).*
Calon et al. ("Docosahexaenoic acid protects from dendritic pathology in an Alzheimer's disease mouse model." Neuron 43.5 (2004): 633-645).*
Christensen et al., "Intestinal Absorption and Lymphatic Transport of Eicosapentaenoic (EPA), Docosahexaenoic (DHA), and Decanoic Acids: Dependence on Intramolecular Triacylglycerol Structure", Am J Clin Nutr, 1995, 61, 56-61.
Banno, Fumiaki et al., "Lymphatic absorption of docosahexaenoic acid given as monoglyceride, digiyceried, triglyceride, and ethyl ester in rats", Medline, Feb. 2002, 34.
Colquhoun, A A et al., "Gamma-Linolenic acid and eicosapentaenoic acid induce modifications in mitochondrial metabolism, reactive oxygen species generation, lipid peroxidation and apoptosis in Walker 256 rat carcinosarcoma cells", Biochimica and Biophysica Acta. Molecular and Cell Biology of Lipids, Elsevier, Amsterdam, NL, Oct. 31, 2001, 1533(3), 207-219.
Database WPI Week 199722, Derwent Publications Ltd., London, 1997, XP002426911 & Patent abstracts of Japan for JP 0907782 a (Asahi Kasei KK) Mar. 25, 1997 abstract.
Gohil, K., et al., "Blood glutathione oxidation during human exercise", J. Appl. Physiol, 1988, 64(1), 115-119.

(Continued)

Primary Examiner — Layla Soroush
(74) Attorney, Agent, or Firm — Baker & Hostetler LLP

(57) ABSTRACT

The present invention relates to the use of an acid enriched in docosahexaenoic acid (DHA) or eicosapentaenoic acid (EPA) or DHA-derived EPA for manufacturing a drug for the treatment of processes that involve associated oxidative damage. In particular, it is for the treatment of processes associated with neurodegenerative, ocular, ischaemic and inflammatory pathology, atherosclerosis, with oxidative damage to DNA and with physical exercise.

26 Claims, 27 Drawing Sheets

(56) References Cited

OTHER PUBLICATIONS

Gunstone, "Structured and Modified Lipids—Chapter 12: Fish Oils as Sources of Important Polyunsaturated Fatty Acids"; Gudmundur G. Haraldsson et al., Apr. 27, 2001, pp. 313-350.

Jaescchke, H., "Mechanisms of oxidant stress-induced acute tissue injury", Proc. Soc Exp Biol. Med, 1995, 209, 104-111.

Lew, H. et al., "Changes in the glutathione status of plasma, liver and muscle following exhaustive exercise in rats", FEBS Lett, 1985, 185(2), 262-266.

Lovlin, R. et al., "Are indices of free radical damage related to exercise intensity", Eur. J. Physiol. Occup. Physiol, 1987, 56(3), 313-316.

McPhail, D.B. et al., "Adaptation of the blood antioxidant defence mechanisms of sheep with a genetic lesion resulting in low red cell glutathione concentrations", Free Radic Res Commun., 1993, 18(3), 177-181.

Mora and Pessin, "The MEF2A isoform is required for striated muscle-specific expression of the insulin-responsive GLUT4 glucose transporter", J.Biol. Chem., 2000, 275(21), 19323-16328.

Patent abstracts of Japan for JP 0907782 a (Asahi Kasei KK) Mar. 25, 1997 abstract.

Raastad et al., "Omega-3 fatty acid supplementation does not improve maximal aerobic power, anaerobic threshold and running performance in well-trained soccer players", Scand J. Med Sci Sports, 1997, 7(1), 25-31.

Rotstein et al., "Protective effect of docosahexaenoic acid on oxidative stress-induced apoptosis of retina photoreceptors", Invest. Ophthalmol. Vis Sc., May 2003, 44(5), 2252-2259.

Scientific Committed on Food, Composition and specification of food intended to meet the expenditure of intense muscular effort, especially for sportsmen, www.ec.europa.eu/food/fs/sc/scf/out65_en.pdf, Feb. 28, 2001.

Senanayake et al., Incorporation of docosahexaenoic acid (DHA) into evening primrose (Oenothera biennis L.) oil via lipase-catalyzed transesterification, Food Chemistry, 85, 2004, pp. 489-496.

Sen, C.K. et al., "Exercise-induced oxidative stress: glutathione supplementation and deficiency", J. Appl. Physiol, 1994, 77(5), 2177-2187.

Watkins, Steven M. et al., "Docosahexaenoic acid accumulates in cardiolipin and enhances HT-29 cell oxidant production", Journal of Lipid Research, Aug. 8, 1998, 39(8), 1583-1588.

Banno, et al., "Lymphatic Absorption of Docosahexaenoic Acid Given as Monoglyceride, Diglyceride, Triglyceride, and Ethyl Ester in Rats", J. Nutr. Sci Vitaminol, vol. 48, 2002, 30-35.

Chauvin Bausch & Lomb, Letter from Associate, Dated Apr. 22, 2004, 1 pg.

Delcourt, "Ceil, Stress Oxydant et Nutrition", Actualites sur la Micronutrition Oculaire, Mar. 3, 2004, 14-18.

Elner, "Retinal Pigment Epithelial Acid Lipase Activity and Lipoprotein Receptors: Effects of Dietary Omega-3 Fatty Acids", Trans Am Ophthalomol Soc., 2002, 301-338.

Fevrier, "Etude de Reactions d' Esterification Enzymatiques par des Lipases. Application a la Synthese en deux etapes d'un Triglyceride Structure, le 1,3-dicaprylyl-2-linoleylglycerol", Pierrick Fevrier PhD Dissertation, Dec. 6, 2001, 5 pgs.

Haraldsson, et al., "The Synthesis of Homogeneous Triglycerides of Eicosapentaenoic Acid and Docosahexaenoic Acid by Lipase", vol. 51(3), 1995, 941-952.

Iraz, et al., "Omega-3 Essential Fatty Acid Supplementation and Erythrocyte Oxidant/Antioxidant Status in Rats", Annals of Clinical & Lab. Science, vol. 35(2), 2005, 169-173.

Nieto, et al., "Preparation of sn-2 Long-Chain Polyunsaturated Monoacylglycerols from Fish Oil by Hydrolysis with a Stereo-Specific Lipase from Mucor Miehei", Grasas y Aceites, vol. 50(2), 1999, 111-113.

Pronova Biocare, "Research, Purity and Efficacy Underscore Commitment to the Marine Omega-3 Category", Natural Products Industry Insider, 2004, 9 pgs.

Rotstein, et al., "Protective Effect of Docosahexaenoic Acid on Oxidative Stress-Induced Apoptosis of Retina Photoreceptors", Investigative & Visual Science, vol. 44(5), May 2003, 2252-2259.

Shimada, et al., "Production of Functional Lipids Containing Polyunsaturated Fatty Acids with Lipase", Enzymes in Lipid Modification, 2000, 128-147.

Souied, "Omega-3 et DMLA", Actualites sur la Micronutrition Oculaire, 3, Mar. 3, 2004, 46-56.

* cited by examiner

ABSOLUTE CONSUMPTION OF OXYGENE IN THE VENTILATORY THRESHOLD 2

CARDIAC FREQUENCY IN THE VENTILATORY THRESHOLD 2

USE OF DHA, EPA OR DHA-DERIVED EPA FOR TREATING A PATHOLOGY ASSOCIATED WITH CELLULAR OXIDATIVE DAMAGE

CROSS REFERENCE TO RELATED APPLICATIONS

The present application is a divisional of pending U.S. patent application Ser. No. 12/158,205, filed Jun. 19, 2008, which is a 371 application of PCT/EP2006/070016, filed Dec. 20, 2006, which claims priority to Spain Application Nos. P-200503202 filed Dec. 21, 2005, P-200602417 filed Sep. 25, 2006, P-200602418 filed Sep. 25, 2006, and P-200603231 filed Dec. 20, 2006, each of which is hereby incorporated by reference in its entirety.

FIELD OF THE INVENTION

The present invention relates to the use of an acid enriched in docosahexaenoic acid (DHA) or eicosapentaenoic acid (EPA) or DHA-derived EPA for manufacturing a drug for the treatment of processes that involve associated oxidative damage.

BACKGROUND OF THE INVENTION

The omega-3 fatty acids are necessary for maintaining cellular functional integrity, and are necessary in general for human health. Docosahexaenoic acid (22:6 n-3, DHA), an important omega-3 component of fish oil and of marine algae, is concentrated in the brain, in the photoreceptors and in the synapses of the retina. DHA-enriched diets are initially metabolised by the liver and afterwards distributed via the lipoproteins in the blood in order to meet the needs of the various organs. The administration of DHA leads to an increase of its concentration at tissue level, inducing also an increase in the concentration of omega-3 eicosapentaenoic acid (EPA) which in linked metabolically, whereas the administration of EPA only increases its concentration decreasing that of DHA at cell level.

In general, the DHA is incorporated into the phospholipids of the cell membrane, which have effects on its composition and functionality, on the production of reactive oxygen species (ROS), on membrane lipid oxidation, on transcription regulation, on the biosynthesis of eicosanoids and on intracellular signal transduction. Furthermore, in the central nervous system, the DHA is involved in the development of the learning capacity related to the memory, in the excitable functions of the membrane, in biogenesis of the photoreceptor cells and in transducing the signal dependent upon quinase protein. A potential dietary therapy would be based on correcting the optimum levels of omega-3 fatty acids to prevent certain pathologies from originating or progressing, such as inflammatory pathologies, tumoral processes, cardiovascular diseases, depression and neurological disorders.

In the central nervous system, both the brain and the retina show an unusual capacity for retaining DHA, even under situations of very prolonged dietary deficiencies of omega-3 fatty acids. Several studies have described the protective effect of DHA on neurones, in which it is present in very high levels. For example, it is involved in protecting the neuronal cells from death by apoptosis. Recently, it has been shown that DHA, found in reduced amounts in the hippocampus of rats of advanced age, is capable of protecting primary cultures of said cells against the cytotoxicity induced by glutamate.

In the photoreceptors of the retina, DHA has also been shown to modulate the levels of the pro- and anti-apoptotic proteins of the Bcl-2 family. The external segments of the retinal photoreceptor contain rodopsin, as well as a higher DHA content than any other type of cell. The DHA is concentrated in the phospholipids of the photoreceptor segment disc's outer membranes. Retinal dysfunctions have been observed under conditions of reduction of optimal DHA concentration. The retina pigmentary epithelial cell (RPE) plays a very active role in DHA take-up, conservation and transport. The high DHA content in the photoreceptor and in the RPE cells is mainly linked to domains in the membrane with physical characteristics that contribute to the modulation of receptors, ionic channels, carriers, etc., while it also appears to regulate the concentration of phosphatidilserine.

It is unknown to date if these effects are entirely mediated by the DHA itself or by any metabolic derivatives. Certain derivatives of DHA have been identified in the retina. Although the enzymes involved in the synthesis of said derivatives have not been identified precisely, some recent results suggest the participation of an $A_2$ phospholipase (PLA$_2$) followed by a lipoxygenase (LOX). The PLA$_2$ releases the DHA from the membrane phospholipids and the LOX converts it into its metabolically active derivatives.

The reactive oxygen species (ROS) are produced during normal cellular functioning. The ROS include the superoxide anion, hydrogen peroxide and the oxydril radical. Their high chemical reactivity leads to the oxidation of proteins, of DNA or of lipids. The superoxide dismutase (SOD), the catalase (CAT) and the glutation peroxidase (GPx) are the primary antioxidant enzymes that protect against the molecular and cellular damage caused by the presence of ROS. The oxidative stress activates many metabolic channels; some are cytoprotective, while others lead to death of the cell. Recent studies indicate that an imbalance between ROS production and breakdown is a significant risk factor in the pathogenesis of many illnesses, in some cases related to a deterioration of the antioxidant system.

The DHA is presented as a target of the ROS that produces damage to the cell of the photoreceptor and to the RPE. The retinal degeneration induced by light promotes loss of DHA in the photoreceptors. For example, when the RPE cells are damaged or die, photoreceptor function deteriorates because the RPE cells are essential for its survival. Thus, death of the RPE cell under the effect of oxidative stress leads to a deterioration of eyesight, particularly when the cells of the macula are affected, since it is responsible for eyesight acuity. The pathophysiology of many retinal degenerations (e.g., macular degenerations related to age and to Stargardt disease) involves oxidative stress that leads to RPE cell apoptosis. Indeed, RPE cell apoptosis appears to be the dominant factor in the macular degeneration observed with age. Such studies suggest that said cells have developed highly effective antioxidant mechanisms to protect themselves from their high DHA content and show notable adaptive capacity.

Furthermore, the relationship between the free radicals and ageing is perfectly well accepted, based on the evidence that free radicals produced during aerobic respiration cause oxidative damage that accumulates and leads to a gradual loss of the homeostatic mechanisms, interference in gene expression patterns and a loss of the cell's functional capacity, leading to ageing and death. An interrelation exists between the generation of oxidants, antioxidant protection and repair of the oxidative damage. Many studies have been carried out to determine whether antioxidant defences decline with age. These have included analysis of the main components thereof: activity or expression of the SOD, CAT, GPx enzymes, glutation reductase, glutation-S-transferase and the concentration of compounds of low molecular weight with antioxidant properties. For example, an over-expression of SOD and CAT in *Drosophila melanogaster* increases life expectancy by 30% and reduces damage by protein oxidation. In this context, in vitro and in vivo exposure of cutaneous tissue to UV rays generates free radicals and other reactive oxygen species, leading to cellular oxidative stress, documented as contributing significantly to ageing. Excessive exposure of the skin to ultraviolet radiation can give rise to acute or chronic damage. Under acute conditions erythema or burns can be produced, while chronic over-exposure increases the risk of skin cancer and ageing. Moreover, it is known that the cutaneous cells can respond to acute or chronic oxidative stress by increasing expression of a variety of proteins, such as the enzymes involved in maintaining cell integrity and resistance to oxidative damage.

In the art, it is well known that telomeres are non-coding DNA regions located at the ends of eukaryotic chromosomes. These are constituted by highly conserved DNA sequences, repeated in tandem $(TTAGG)_n$ and associated proteins, and have a special structure which hinders the ligation to the ends of other chromosomes, preventing the telomeric fusion. They have an essential role in the preservation of the chromosomic integrity, protecting the coding DNA from the enzymatic action and its degradation, contributing to the maintenance of the chromosomic stability.

In contrast with coding sequences which have a semiconservative replication, the telomeres undergo a progressive loss of its repetitive sequences during the successive cell division. Nowadays, it is considered that a minimum telomeric length is required in order to keep the telomere function and when these reach a critical size they have difficulties for the division in the mitosis, generating telomeric association (TAS) and chromosomic instability. Said chromosomic instability would be associated with an increase in the probability of producing errors capable of generating significant genetic changes.

Owing to the multiplicity of double bonds, the omega-3 fatty acids are considered to be molecular targets for generation and propagation of free radicals during the oxidative stress processes related to generation of lipidic peroxides. Contradictory results have been obtained, however, in various studies of susceptibility to oxidative stress owing to dietary supplements of omega-3 fatty acids. Some studies in humans have shown increased oxidation of the LDL, while others have found no such effect. In studies with animals, treatment with omega-3 fatty acids has been found to lead to increased or reduced susceptibility to oxidation of the LDL. On the other hand, an over-expression of the genes involved in the antioxidant defence system has been found in the livers of mice fed on a fish-oil-enriched diet for three months.

Furthermore, various in vitro studies with a cellular line of glyal origin have shown that membranes rich in omega-3 fatty acids are more susceptible to oxidative damage. Long-term supplementation of these cells with high concentrations of DHA resulted in increased levels of lipidic peroxides in the culture medium, and a higher percentage of cell death due to apoptosis induced by exposure to hydrogen peroxide. It has also been shown, however, that intra-amniotic administration of ethyl docosahexaenoate reduces lipidic peroxidation in the foetal brains of rats. It has been suggested that this response is due to a free-radical sequestering effect via activation of antioxidant enzymes. An increase in the antioxidant capacity of the brain is important for the primary endogenous defence against oxidative stress, because the brain is relatively rich in polyunsaturated fatty acids and relatively poor in antioxidant enzymes.

These contradictory results suggest that the hypothesis based on the premise that oxidation of a fatty acid increases with the number of double bonds has no in vivo applicability, since other potential mechanisms may act to reduce oxidative damage, such as a three-dimensional structure of the omega-3 fatty acids in the lipids and lipoproteins of the membrane that make the double bonds less susceptible to an attack by the ROS, an inhibition of pro-oxidant enzymes such as $PLA_2$ or a greater expression of antioxidant enzymes.

On the other hand, the idea of associating physical exercise with the production of free radicals comes from early 80s due to the observation of the damage in membrane lipids during ischemia-reperfusion events in hypoxic tissue (see Lovlin et al., *Eur. J. Appl. Physiol. Occup. Physiol.* 1987, 56 (3) 313-6). At the same time, an increase in the GSSH/GSH ratio was observed in rat muscle cells (see Lew H. Et al. *FEBS Lett*, 1985; 185(2): 262-6, Sen C K et al., *J. Appl. Physiol.* 1994; 77(5): 2177-87) as well as in human blood (see MacPhail Db et al., Free Radic Res Commun 1993; 18(3): 177-81, Gohil K. et al. J. Appl. Physiol. 1988 January; 64(1): 115-9). Free radicals also affect DNA and acute physical exercise increases damage in DNA, as evidenced by the increase of 8-OxodG. Exhausting physical effort (running a marathon) causes damage in DNA which is evident for some days after the trial and also causes damage in immunocompetent cells (which can be associated with the immune decrease shown in sportsmen after such a trial).

However, other authors did not observe any effects (except for minor damage) after swimming for 90 minutes, running for 60 minutes or making an exhausting effort by rowing. At the same time, researches on trained and non-trained sportsmen did not find any difference in the urinary excretion of 8-oxo-dG, even those finding such a damage, considered to be secondary to subsequent reactions to the effort and not to the action of exercise over the DNA in acute way.

The event of intensive physical exercise producing oxidative stress is very well known in the art, but its origin is not well determined yet.

Studies carried out with n-3 fatty acids related to sports performance were focused on the antiinflammatory effect and, indeed, first assays tried to find the possible action of these nutrients improving the alveolar-capillary absorption by diminishing the intensive physical exercise-induced broncoconstriction. In that regard, Mickleborough proved that after administering 3.2 g EPA and 2.2 g DHA regime proinflammatory cytokines were attenuated by diminishing the presence of TNF-α and IL-1β in an elite athlete, along with a decrease in the broncoconstriction. Walser related n-3 fatty acids vascular effects to positive effects in people showing intolerance to physical exercise. In that regard, van Houten et al. studied that a n-3 fatty acid high ingestion was associated with a better recovery in patients carrying out a cardiac rehabilitation after a coronary syndrome.

The absence of positive results in the physical performance in the analyzed studies is due to the evaluation of patients, not healthy people, and what it has been searched are vascular and inflammatory effects.

At the same time, researches have been carried out based on the following theoretical concept: increasing free fatty acids in plasma above 1 mmol/L (occurring when glycogen is used up), the competence with tryptophan transport makes this to be increased with the subsequent serotonine increase, a neurotransmitter related to the so-called "central fatigue" in long duration sports. In that regard, it is known that n-3 fatty acids diminish the amount of free fatty acids in plasma probably by up-regulating the fatty acid oxidation by activating the transcription nuclear factor PPARα. However, these assays were not successful, since Huffman (2004) by using a dose regime of 4 g of n-3 fatty acid (500 g capsules containing 300 mg EPA and 200 mg DHA) carried out a study in both sex runners without finding any decrease in free TRP nor a less perception of effort, nor any statistically performance increase in the performance, although there was a statistical tendency for improving the performance in subjects whom n-3 fatty acid were administered, leaving open the possibility to authors that the cause of diminishing the statistical power for the study was the low number of subjects studied (5 men and 5 women).

Another subsequent research wherein the efficacy of n-3 acids related to the performance was evaluated did not find any significant differences using maize oil as a placebo. Raastad administering 1.60 g EPA and 1.04 g DHA per day for several weeks, did not find any improvement in football players (see, Raastad et al. Scand J. Med Sci Sports 1997; 7(1): 25-31).

On the other hand, it is known that free fatty acids interfere with the use of glucose in the muscle, since its analogues at intracellular level, acyl-CoA, in the mitochondria inhibit the pyruvate dehydrogenase (inhibition by product), furthermore, stimulates glycogenolysis and glyconeogenesis, causing a smooth hyperglycemia during fasting, indeed, the continuous administration of polyunsaturated fatty acids during fasting helps to maintain glycemia, by maybe activating glucose-6-phosphatase at a hepatic level. It is also known that a composition of fatty acids in the muscle alters insulin sensitivity, showing that a high content of polyunsaturated fatty acids in plasmatic membrane improves insulin sensitivity and a high content of saturated fatty acids produces the opposite effect.

Exercise increases glucose uptake, capillary perfusion, glycogen synthesis rate and insulin sensitivity. During muscular contraction changes are produced in temperature, intracellular pH, ATP/ADP ratio, as well as $Ca^{++}$ intracellular concentration and other metabolites which could act as messengers in the cellular functioning regulation with exercise. In this regard, $Ca^{++}$ regulates a great amount of intracellular proteins, including calmodulin kinase, protein kinase C(PKC) and calcineurin which are important intermediates in the signals of intracellular transduction. During aerobic exercise, acetyl-CoA carboxylase is deactivated by AMP kinase (AMPK) which leads to a drop in malonyl-Coa levels, deinhibiting carnitine palmitol transferase with the resulting increase of fatty acid transport within the mitochondria (thus promoting fatty acid oxidation).

AMPK activation effects probably include stimulation of GLUT4 and hexokinase expression, as well as mitochondria enzymes. However, surprisingly, AMPK activation is not the unique way (independent of insulin) wherein the exercise increases the response to glucose in skeletal muscle. See Mora and Pessin, *J. Biol. Chem.* 2000; 275 (21): 16323-16328, showed that an increase in the glucose response in the muscle, indeed, there are several transcription factors such as MEF2A and MEF2D activating GLUT4 and those factors are activated by exercise.

An increase in intramuscular lipids is common in obesity states and physical training, but the result is that for obese people is associated with insulin resistance, whereas in sportsmen the great activity of carnitine palmitol transferase makes fatty acids undergo beta oxidation. There are strong evidences that a rich diet in n-3 fatty acid, even with an increase of glycemia and insulinaemia (signals of insulin resistance), act at a insulin receptor level maintaining the level of GLUT-4 protein translocation, which has specifically showed with DHA (see, Jaescchke H. Proc. Soc Exp Biol. Med 1995; 209: 104-11).

DESCRIPTION OF THE INVENTION

The present invention concerns the unexpected discovery that the administration of docosahexaenoic acid (herein also referred to as DHA) or eicosapentaenoic acid (EPA) or DHA-derived EPA, whether in free form or incorporated into a triglyceride, among others, acts as a cellular antioxidant.

In this way and taking into account the metabolic relation between DHA and EPA (retroconversion of DHA to EPA), all effects disclosed observed previously for the administration of DHA must be applicable to mixed systems DHA/EPA or even to monocomponent systems of EPA, even though EPA is not named specifically.

An object of the present invention is therefore the use of docosahexaenoic acid for the manufacturing of a pharmaceutical composition for the treatment of cellular oxidative damage.

Another object of the present invention is the use of docosahexaenoic acid (DHA) at a specific position of the glycerol backbone, the two remaining positions of the glyceride being also specified in their composition for the treatment of cellular oxidative damage.

A further object of the present invention is the use of docosahexaenoic acid (DHA) for manufacturing a composition for the treatment of the cellular oxidative damage at DNA level. In particular, the use of docosahexaenoic acid has the application as a protective agent in the natural process of telomere shortening and as an inhibitory agent of premature senescence in a treatment of cellular oxidative damage.

It is also an object of the present invention the use of docosahexaenoic acid for manufacturing a composition for the treatment of cellular ageing and hereditary pathologies associated with disorders in the mitochondrial respiratory chain, as well as a composition for treating Down's Syndrome.

A further object of the present invention is the use of docosahexaenoic acid (DHA) for manufacturing a composition for the treatment of the cellular oxidative damage associated with physical exercise. In particular, the use of docosahexaenoic acid has application as an enhancer agent in the sports performance and as a regulating agent of blood glucose levels during physical effort.

It is also an object of the present invention the use of docosahexaenoic acid for manufacturing a composition for enhancing sports performance, as well as a composition for maintaining blood glucose levels after physical exercise by means of, mainly, the administration of a food, a dairy product or any suitable administration form typically used by people when doing physical exercise.

In the present invention, the expression "cellular oxidative damage" means any process that involves an imbalance between the generation and degradation of cellular oxidant species of endogenous or exogenous origin.

Surprisingly, the inventors of the present invention have found that DHA is capable of inhibiting the production of reactive oxygen species (ROS), whether related to a dependent induction of peroxides or superoxides. More specifically, it reduces the production of superoxide anion and therewith of all the derived species produced in the oxidative cascade, such as for example a highly significant reduction of lipidic peroxidation. Furthermore, an increase in antioxidant enzyme activity was found, which suggests an adaptation of the cell by inducing the expression of antioxidant agents, basically enzymes, and by repressing the expression of pro-oxidant agents such as the $A_2$ phospholipase.

In one embodiment of the present invention, said docosahexaenoic acid is incorporated into a monoglyceride, diglyceride, triglyceride, phospholipid, ethyl ester or free fatty acid. Preferably, said docosahexaenoic acid is incorporated into a triglyceride.

In the present invention, "docosahexaenoic acid incorporated into a glyceride" is taken to mean a monoglyceride, diglyceride, triglyceride, phospholipid, with at least one of the three positions esterified with a docosahexaenoic acid and, optionally, at least one of the remaining esterified positions further with one acid selected from a short-, mid- or long-chain fatty acid and a phosphoric acid. Preferably, said glycerol is a triglyceride.

The choice of triglyceride as chemical structure of the DHA is based on data taken from a study which compared the bioavailability of four omega-3 acid concentrates in the form of ethyl esters, phospholipids, free fatty acids and triglycerides following oral administration, which demonstrated that the re-esterified triglycerides presented a higher bioavailability than the other preparations.

In a preferred embodiment of the present invention, said docosahexaenoic acid is found in a percentage by weight of between 20 and 100% in relation to the total fatty acids, preferably between 40 and 100% in relation to total fatty acids, and more preferably said docosahexaenoic acid is in a percentage by weight between 66 and 100% in relation to total fatty acids.

In another preferred embodiment, said docosahexaenoic acid is incorporated into at least one specific position of a glycerol via an ester bound, a structured lipid, for manufacturing a pharmaceutical composition for the treatment of cellular oxidative damage.

Such a glycerol may further comprise at least one fatty acid and/or one phosphoric acid so that said docosahexaenoic acid being incorporated into a position selected from sn-1, sn-2 and sn-3, may further comprise, optionally, at least one acid selected from a short- and/or mid-chain fatty acid and a phosphoric acid, and when incorporated into the sn-2 position may further comprise, optionally, at least one acid selected from a fatty acid and a phosphoric acid.

In this regard, when referring to the term optionally, it should be understood that said docosahexaenoic acid incorporated into a position selected from sn-1, sn-2 and sn-3 may or not further comprise at least one acid selected from a short- and/or mid-chain fatty acid and a phosphoric acid, or otherwise that said docosahexaenoic acid incorporated into the sn-2 position may or not further comprise at least an acid selected from a long-chain fatty acid and a phosphoric acid.

Surprisingly, the inventors of the present invention have found that the use of structured glycerols wherein the position of the docosahexaenoic acid has been selected and the composition of the rest of the compound bound to the glycerol, leads to an unexpected increase, at least twice or even thrice, the therapeutic efficiency of the use of docosahexaenoic acid for manufacturing a pharmaceutical composition for the treatment of cellular oxidative damage.

The common definition relates to fats containing fatty acids located in specific positions in the glycerol backbone. By similarity with the in vivo fatty acid biodistribution, the long-chain polyunsaturated fatty acids (PUFAs) are located preferably in the sn-2 position of the glycerol and taking into account the intestinal absorption process, triglycerides are hydrolized by lipases to free fatty acids, di- and monoglycerides, from which the free fatty acids and sn-2 monoglycerides are absorbed directly by intestinal epithelial cells, named enterocytes.

By using docosahexaenoic acid incorporated into a specific position of the glycerol backbone, via an ester bound, provides an increased bioactivity, an increased antioxidant protection at the same molar percentage in respect with the whole amount of fatty acids present and a diminished dependency on the administration dosage in respect with the antioxidant effect of the docosahexaenoic acid in the glyceride.

Advantageously, the inventors of the present invention have found that the use of docosahexaenoic acid incorporated into a position of the glycerol selected from sn-1, sn-2 and sn-3, and optionally said glycerol further comprising at least one acid selected from a short- and/or mid-chain fatty acid and a phosphoric acid, provides an increased bioactivity, an increased antioxidant protection at the same molar percentage in respect with the whole amount of fatty acids present and a diminished dependency on the administration dosage in respect with the antioxidant effect of the docosahexaenoic acid in the glycerol.

Also advantageously, the inventors of the present invention have found that the use of docosahexaenoic acid incorporated into a sn-2 position of a glycerol and optionally said glycerol further comprising at least one acid selected from a long-chain fatty acid and a phosphoric acid, provides also an increased bioactivity, an increased antioxidant protection at the same molar percentage in respect with the whole amount of fatty acids present and a diminished dependency on the administration dosage in respect with the antioxidant effect of the docosahexaenoic acid in the glycerol.

Preferably, acids also present in a glycerol with the docosahexaenoic acid will be short-chain fatty acids (C1-C8) or mid-chain fatty acids (C9-C14) or a phosphoric acid, since these have no functional activity, but only energetic activity and, therefore, will not compete with the docosahexaenoic acid.

Therefore, still more preferably, the present inventions relates to the use of docosahexaenoic acid incorporated into a glycerol wherein one of the positions sn-1 and sn-3 are free or occupied by a mid-chain fatty acid (C9-C14) or short-chain fatty acid (C1-C8) or a phosphoric acid and in which sn-2 position is occupied by functional DHA. Thus, a still higher increase of DHA is achieved since it is more efficiently absorbed in the intestinal cells.

Therefore, the synthesis of structured glycerides wherein the docosahexaenoic acid has been incorporated into any position of the glycerol when it does not compete with other fatty acids and wherein the DHA has been incorporated into the sn-2 position of the glyceride when it competes with at least one fatty acid, shows improvements related to its antioxidant effect and, therefore, it is a preferred way for manufacturing a composition for the treatment of the oxidative cellular damage.

The inventors of the present invention have found that a cell enriched with a composition with DHA, in accordance with the invention, is better prepared to face up to a new situation of oxidative stress and thus to minimise the adverse effects that can derive therefrom. That is, the presence of the DHA in the biomembranes induces a cellular adaptive response to the oxidative stress. Adaptive response is a cellular phenomenon by which exposure to a toxic agent (in sub-lethal concentrations) provokes a cellular response which will subsequently protect the cell against the deleterious effects of that same toxic agent at lethal concentrations, or, put another way, it is a beneficial effect unleashed by a low level of exposure to an agent that is harmful at high levels.

Administration of DHA has the following substantial advantages:

a) Increased cellular antioxidant activity;
b) Absence of cellular cytotoxicity at the dosages administered;
c) Absence of significant alterations to cellular oxidant status at the dosages administered;
d) Adaptive cellular antioxidant activity.

Due to all the above, in a preferred embodiment the present invention relates to the use of docosahexaenoic acid for manufacturing a pharmaceutical composition for treating a pathology associated with cellular oxidative damage, said pathology being a neurodegenerative pathology, preferably selected from the group that comprises: multiple sclerosis, Alzheimer's disease, Parkinson's disease, amiotrophic lateral sclerosis and muscular dystrophy, among others.

In another embodiment of the present invention, the pathology associated with the oxidative damage is an ocular pathology, preferably one selected from the group that comprises pigmentary retinosis, macular degeneration and cataracts, among others.

In yet another embodiment, the pathology associated with the oxidative damage is an ischaemic pathology, particularly a myocardial infarct, cerebral infarct, etc.

In yet another embodiment of the present invention, the pathology associated with the oxidative damage is an inflammatory process, preferably selected from the group comprising arthritis, vasculitis, glomerulonephritis and eritomatose lupus, among others.

In another preferred embodiment, the pathology associated with the oxidative damage is atherosclerosis.

Another aspect of the present invention is the use of DHA as a protective agent in the natural process of telomere shortening and as an inhibitory agent of premature senescence.

The mechanisms producing telomeric associations (TAS) are still unknown but the authors of the present invention suggest that this could be associated with a deficit in the activity of enzyme telomerase which synthesizes the repetitive sequences of DNA characteristic for telomeres, thereby stabilizing the length thereof.

The telomerase is very active in foetal cells, but has not much activity in adult tissue cells. TAS have seldom found in normal cells, but they have been observed in infected cells by virus or tumour cells.

It has been observed that there is a progressive reduction in the number of in vitro telomeric repetitions, as well as in function of cellular ageing, in vivo, which is associated with an inhibition of the telomerase activity in the senescence. Likewise, the authors of the present invention have studied the telomeric length in fibroblasts and lymphocytes from centenary healthy persons, having found a telomeric shortening during the in vitro propagation of the fibroblasts, as well as a reverse correlation between the telomeric lengths and the donor's age.

Although the telomere shortening occurs naturally with the cellular replication, a premature senescence and breakages of telomeres when inducing oxidative damage in the DNA have been observed. The telomeres are more sensitive to oxidative damage and their breakages are less efficiently repaired than other parts of the genome. This leads to an accumulation of telomeric damage which produces a faster shortening during the DNA replication reducing the cellular replicative life expectancy. The reactive oxygen species (ROS), particularly superoxide anions, hydrogen peroxide and oxidril radicals, can accelerate the losses in the telomeres during the replication of some cellular types, even though they also induce premature senescence regardless of the telomere shortening.

Surprisingly, the authors of the present invention have found that the use of docosahexaenoic acid for the treatment of the cellular oxidative damage at DNA level allows to reduce the shortening rate of the telomeres and, therefore, inhibit the cellular senescence.

The present inventors have found a reverse correlation between the shortening rate of telomeres and the cellular antioxidant capacity in more than 20 fibroblasts human strains. Most of the cellular parameters of these prematurely aged fibroblasts are the same as the normal ageing of these cells (morphology, accumulation of lipofuscin and changes in the genic expression). The fibroblasts with a lower antioxidant defence shorten their telomeres faster and vice versa. The shortening rate of the telomere is higher in cells with a lower antioxidant defence. Furthermore, free radical scavengers reduce the shortening rate of the telomere.

These data are in concordance with those showing an important role of the antioxidant enzymes, glutation peroxidase and superoxide dismutase, in the shortening rate of telomeres in human fibroblasts. These dates prove that the length of telomeres is determined mainly by the relation between the oxidative stress and the cellular antioxidant defence capacity. Thus, the length of age-dependent telomeres is an accumulative measurement of the history of the oxidative damage that a cell has undergone along its life.

A correlation between oxidative stress and shortening rate of telomeres has been shown for hereditary pathologies associated with disorders in the mitochondrial respiratory chain and for Down's Syndrome.

Therefore, the existent relation between the oxidative cellular damage in DNA and the telomere shortening and its effect in the cellular senescence allow to use the docosahexaenoic acid as a powerful protective agent in the natural process of telomere shortening and as an inhibitory agent of premature senescence.

On the other hand, the use of enzymes for the production of omega-3 fatty acid-enriched oils has several advantages in respect with other methods based on chemical synthesis and subsequent processes of purification (chromatographical separations, molecular distillation, etc.). The latter require extreme conditions of pH and high temperatures which could partially destroy all double bounds all-cis of omega-3 PUFAs by oxidation, by cis-trans isomerization or migration of double bound. The soft conditions used in enzymatic synthesis (temperature lower than 50° C., pH 6-8 and less chemical reagents) provides a synthetic alternative conserving the original structure of omega-3 PUFAs with an increase in the structural selectivity in the acylglycerides, considered to be the most favourable chemical structure from a nutritional point of view.

The pharmaceutical composition comprising DHA can be found in the form of an oil or an emulsion, which can be administered by oral, sublingual, intravenous, intramuscular, topical, subcutaneous or rectal routes, or even by merely bringing the active ingredient of the microemulsion of the invention in liquid or vapour form into contact with the olfactory organs situated at the entrance of the respiratory tracts. Thus, the administration can be carried out by spraying, misting or atomisation of the microemulsions or by inhalation.

Optionally, said pharmaceutical composition further comprises a second active ingredient.

Similarly, the pharmaceutical composition comprising DHA can be used in the food industry for the purpose of enriching food products (e.g. lactic products such as yoghurts, milk, etc) with a natural antioxidant agent such as DHA.

Therefore, in another embodiment of the present invention said pharmaceutical composition is administered to a patient who is already receiving a treatment against a pathology associated with oxidative damage.

Another object of the present invention is the use of DHA as an enhancer agent in the sports performance and as a regulating agent of blood glucose levels during physical effort.

In this way, the authors of the present invention have surprisingly found that the use of said docosahexaenoic acid during physical exercise leads to an increase in the sports performance maintaining blood glucose levels (glycemia) after such physical exercise (without administering carbohydrates).

On this context of the present invention, by "amateur" or "non-competing sportsmen" is taken to mean any person doing physical exercise in a sporadic way and non-professionally. And by "competing sportsmen" or "trained sportsmen" is taken to mean any person doing physical exercise in a regular way and/or at professional level. Likewise, the terms "physical exercise" and "physical effort" are used in an equivalent and exchangeable way, as well as the term "sportsmen" is used for men and women.

Sports Performance

In order to evaluate sports performance there are several parameters which allow to give a valoration about the improvement of such a sports performance.

In sportsmen doing aerobic sports an increase in the performance is considered when there is an increase of the percentage of oxygen maximum consumption % $VO_{2max}$ in the UV 2 (anaerobic threshold), since $VO_2$max hardly increases during a competitive season in very well trained sportsmen. Little changes in the percentage of $VO_{2max}$ in the threshold are data directly related to an increase in the performance.

The present inventors have shown that a statistically significant increase of the oxygen consumption ($VO_2$), both absolute ($p<0.019$) and relative ($p<0.036$) values to the weight in the ventilatory threshold 2 when comparing basal triangular effort trials with those carried out after four months of treatment with DHA. The increase of this parameter is shown for both competing cyclists ($p<0.047$) and non-competing cyclists, being the difference in the latter non statistically significant (FIG. 24)

Another parameter related to an increase in the sports performance is the increase in the cardiac frequency wherein the UV2 of the effort trial is set, since in case the cardiac frequency increases in the anaerobic threshold, the sportsmen are considered to be capable of slightly increasing its ability of keeping the aerobic metabolism in higher intensities. The present inventors have observed an increase in the cardiac frequency in UV2 for $p=0.082$ when comparing said parameter obtained in the basal trial with that obtained in the triangular trial after 4 months consuming DHA. These dates are notably shown ($p<0.017$) in the subgroup of cyclists with a high competitive level (FIG. 25).

In this regard, there is an increase in the time needed to reach the statistically significant UV2 (FIG. 26).

Finally, the cardiac frequency for the same effort level is lower if sportsmen are aerobically trained. The present inventors have seen that in cyclists being administered with DHA cardiac frequency decreases in a statistically significant way ($p<0.043$) when comparing these data for both trials at the point when sportsmen consume 2000 ml $O_2$/min (FIG. 27)

It can be concluded from these studies that in sportsmen taking DHA for 4 months an increase in the consumption of oxygene, absolute and relative, in the UV2 ($p<0.008$ and $p<0.015$, respectively), an increase in the charge corresponding to the UV2 ($p<0.063$) and a decrease in the cardiac frequency when sportsmen presents an oxygene consumption of 2000 ml/min ($p<0.062$) have been observed. All these are parameters indicating an increase in the sports performance after taking 2.1 g DHA/24 h (6 capsules of 500 mg at 70% by weight), distributed in 3 daily dose for 4 months. Said quantities are expressed by way of example and non-limitative of the present invention.

Several biochemical variables related to oxidative damage were also analyzed after effort trials.

1.—Plasma Total Antioxidant Capacity (PTAC). There is a general and significant statistically increase of PTAA ($p<0.05$) while carrying out rectangular trials. These increases are higher in sportsmen after being administered DHA for three weeks, both considering as a whole or as competing cyclists, without showing any difference between basal trial and trial realized after consuming DHA for three weeks by amateur sportsmen (FIG. 28)

2.—Malonyldialdehyde (MDA). MDA is the mostly obtained product after reacting lipidic peroxides produced by oxidative stress with thiobarbituric acid. It is shown that a significant increase of oxidative damage to plasmatic lipids while carrying out all effort trials ($p<0.035$). After DHA ingestion for 3 weeks, oxidative damage to lipids while carrying out the effort trial is lower then that at the beginning ($p<0.05$). This difference is much more important for trained sportsmen than for amateur sportsmen (FIG. 29)

3.—8-oxo-7,8-dihydro-2-'-deoxyguanosine (8-oxodG). 8-oxodG is a oxidative stress biomarker. There is an increase of oxidative damage to the DNA while carrying out rectangular effort trials ($p<0.011$). This oxidative damage diminishes after administering DHA for 3 weeks ($p<0.035$). This decrease in the oxidative stress is more important in non-competing cyclists than in competing cyclists, this difference not being statistically significant (FIG. 30)

Glycemia Studies

In order to study blood glucose levels a rectangular effort trial was carried out on a bicycle roller with a maximum charge maintained equivalent to a rate corresponding to 75% of $VO_2$max calculated over the maximum triangular effort trial, maintaining the slope constant at a value of 2%. The time for the trial is 90 minutes and the consumption of water through the same is carried out ad libitum.

Since beverage with carbohydrates were not ingested, an hypoglycemia was expected. This hypoglycemia of second extraction (twenty minutes after the end of the trial in respect to the starting sample obtained twenty minutes before the start), is shown in the first effort trial, as it was expected. However, data obtained after the DHA administration for four months show a statistically significant glycemia maintainement, which was not observed previously and it represents a surprising finding in the realized research.

Generally, a statistically significant decrease ($p<0.0009$) of serum glucose levels throughout rectangular effort trial is observed. However, the behaviour is different depending on the type of sportsmen to be analyzed ($p<0.003$): in the case of usually competing cyclists, there was no significant variation in the decrease of glycemia during the trials, but in case of amateur cyclists, the decrease of glycemia during the basal trial is higher than in usually competing cyclists and after taking DHA for 3 weeks or four months, said decrease virtually disappears (FIGS. 31, 32 and 33).

The existence of normoglycemia during the effort trial at 75% of $VO_2$max for 90 minutes without drinking the beverage with carbohydrates represents a finding which connects the behaviour of DHA during a physical effort with that observed and above-mentioned in relation with the increase of insuline sensitivity. In this regard, Goodyear and Kahn (1998) concluded that the molecular mechanism underlying the response to glucose in the skeletal muscle by insuline or exercise, are different after the publication in 1997 (Winder and Hardie) about the fact AMPK (AMP-activated protein kinase) was high in fibers Iia during exercise, considering that AMPK has a pleiotropic effect inhibiting acetyl-CoA carboxylase and promoting glucose transport among other actions. Perhaps, this may explain the finding about a glycemic response different in sportsmen from that expected according to the studies carried out in sedentary people.

From these studies about the action of DHA over the sports performance and glycemia, it can be concluded the following:

1) It is been proved that the continuous ingestion of DHA for more than 3 weeks produces an increase in the Plasma Total Antioxidant Capacity (PTAC) in a general and statistically significant way ($p<0.05$) in both competitive and amateur cyclists. Also, the oxidative damage to lipids is lower ($p<0.05$) (difference which is more important for trained sportsmen than for amateur cyclists). Finally, it has been shown that the damage to DNA measured by urinary marker (8-oxodG) decreases after taking DHA for three weeks ($p<0.035$).

2) It has been proved that after 4 months of continuous ingestion of DHA, the sports performance is higher (increase of charge and cardiac frequency, as well as the percentage of $VO_2$max in the UV2). Also, a statistically significant normoglycemia in the effort trial for 90 minutes at 75% of $VO_2$max carried out four months later consuming DHA has been observed.

The association of both effects (an enhance in the sports performance and normoglycemia during long period exercise) is a result which was not expected nor known in the art.

Furthermore, it could be concluded that this association of effects is desirable and could be ergogenical aids still not known.

Another object of the present invention is the use of docosahexaenoic acid for manufacturing a composition for enhancing sports performance and maintaining blood glucose levels after physical exercise administered by any suitable means.

It should be considered that the European Union Scientific Committee on Food recommends the following components for a composition of beverage to be taken during a physical exercise (see, http://ec.europa.eu/food/fs/sc/scf/out64_en.pdf).

| 80 kcal/1000 ml | Energy | 350 kcal/1000 ml |
| 20 mmol/l (460 mg/l) | Na$^+$ | 50 mmol/l (1150 mg/l) |
| 200 mOsml/kg water | Osmolarity | 330 mOsml/kg water |

At least 75% of caloric energy must derive from carbohydrates with a high glycemic charge (glucose, maltodextrine, sucrose) Vitamine B1 0.2 mg/100 mg carbohydrates In this regard, the inclusion of carbohydrates is aimed to maintain the glycemia in order to avoid the fast consumption of muscular and hepatic glycogen. It should be considered the drawbacks of gastric emptying diminished due to the increase of osmolarity generating the presence of concentrations of carbohydrates, associated with the feeling of gastric fullness undesirably for a lot of sportsmen. Por consiguiente, preparing a beverage with a loer concentration of carbohydrates by adding DHA could be an ergogenical advantage of undoubted interest in the sports performance.

Accordingly, another aspect of the present invention relates to a pharmaceutical composition comprising DHA which can be used in the in the food industry for the purpose of enriching food products (e.g. dairy products such as yoghurts, milk, etc) with a natural antioxidant agent such as DHA, or further, incorporated into a suitable administration form selected from the group comprising a beverage in all its characteristics for before, during and after physical exercise; energy-giving bar; ergogenical bars; solids and preparations for provisioning; dietetic supplement and polivitaminic preparation (in the form of, for example, capsules, tablets, pills, lyophilised form, or any suitable mean of administration); ergogenical aids; textiles with nanocapsules for skin absorption and any other suitable mean of administration.

KEYS OF THE FIGURES

FIG. 1. Effect of DHA concentration in the Foreskin cells culture medium on the intracellular generation of ROS. The cells were cultured in the presence of a triglyceride with 70% by weight of DHA in relation to the total fatty acids for three days prior to the experiment. (A) ROS detection was carried out with DHR 123 on cells treated with 40 or 60 mM AAPH for 180 min. The data show the mean of three independent experiments. (B) The detection of ROS was carried out with CDCFDA on cells treated with the xanthine/xanthine oxidase system for 180 min. By way of comparison, the data obtained with 100 µM Vitamin E (control) are incorporated. The data represent the mean of three independent experiments.

FIG. 2. Comparative effect of the proportion of DHA of a triglyceride in the Foreskin cells culture medium on the intracellular generation of ROS. (A) The cells were cultured in the presence of each triglyceride for three days prior to the experiment. The concentration on the x-axis is the equivalent that would be obtained with a triglyceride having a DHA content of 70% by weight. The detection of ROS was carried out with DHR 123 on cells treated with 40 mM AAPH for 180 min. The data represent the mean of three independent experiments. (B) Representation of the antioxidant protection in relation to DHA concentration in the oil of 20, 50 and 70%.

FIG. 3. Effect of DHA concentration on the production of TBARS in Foreskin cells. The cells were cultured in the presence of a triglyceride with 70% by weight of DHA in relation to the total fatty acids for three days prior to the experiment at the concentration indicated. The oxidative stress was induced with 40 mM AAPH for 6 h and 24 h of latency. The data represent the mean of three independent experiments.

FIG. 4. Effect of DHA concentration in the Foreskin cells culture medium on the generation of superoxide anions. The cells were cultured in the presence of a triglyceride with 70% by weight of DHA in relation to the total fatty acids for three days prior to the experiment. The detection of superoxide anions was carried out by chemiluminescence immediately following oxidative induction of the cells with 40 mM AAPH and in some experiments in the presence of 10 mM Tyron or of 0.1875 UA/µl of exogenous SOD. The data are representative of three independent experiments.

FIG. 5A. Effect of DHA concentration in the Foreskin cells culture medium on SOD activity. The cells were cultured in the presence of a triglyceride with 70% by weight of DHA in relation to the total fatty acids for three days prior to the experiment at DHA concentrations of 0.5 (A), 5 (B) and 50 µM (C). The SOD activity was analysed indirectly by analysing the decrease in the chemiluminescence generated by the luminol as a consequence of the endogenous SOD activity. Oxidative induction was carried out with the 0.1 mM xanthine/0.005 U/ml xanthine oxidase system that immediately generates superoxide anions. The data are representative of three independent experiments.

FIG. 5B. Effect of DHA concentration in the Foreskin cells culture medium on SOD activity. The cells were cultured in the presence of a triglyceride with 70% by weight of DHA in relation to the total fatty acids for three days prior to the experiment. The SOD activity was evaluated on the non-induced cellular system or the system induced with 40 mM AAPH. The data are representative of three independent experiments.

FIG. 6. Effect of DHA concentration in the Foreskin cells culture medium on GPx activity. The cells were cultured in the presence of a triglyceride with 70% by weight of DHA in relation to the total fatty acids for three days prior to the experiment. GPx activity was evaluated on the non-induced cellular system or the system induced with 40 mM AAPH. The data are representative of three independent experiments.

FIG. 7. Effect of DHA concentration in culture medium of ARPE-19 cells on the intracellular generation of ROS. The cells were cultured in the presence of a triglyceride with 70% by weight of DHA in relation to the total fatty acids for three days prior to the experiment. (A) The detection of ROS was carried out with DHR 123 (A) or with CDCFDA (B) on cells treated with 40 or 60 mM of AAPH for 180 min. The data represent the mean of three independent experiments.

FIG. 8. Comparative effect of DHA concentration of a triglyceride in the culture medium of ARPE-19 cells on the intracellular generation of ROS. The cells were cultured in the presence of each triglyceride for three days prior to the experiment. (A) The concentration on the x-axis is the equivalent that would be obtained with triglyceride having a DHA proportion of 70% by weight. The detection of ROS was carried out with DHR 123 on cells treated with 40 mM de AAPH for 180 min. The data represent the mean of three independent experiments. (B) Representation of the antioxidant protection in relation to DHA concentration in the oil of 20, 50 and 70%.

FIG. 9. Effect of DHA concentration on the production of TEARS in ARPE-19 cells. The cells were cultured in the presence of a triglyceride with 70% by weight of DHA in relation to the total fatty acids for three days prior to the experiment at the indicated concentration. The oxidative stress was induced with 40 mM AAPH for 6 h and 24 h of latency. The data represent the mean of three independent experiments.

FIG. 10. Effect of DHA concentration in the ARPE-19 cells culture medium on the generation of superoxide anions. The cells were cultured in the presence of a triglyceride with 70% by weight of DHA in relation to the total fatty acids for three days prior to the experiment. The detection of superoxide anions was carried out by chemiluminescence immediately following oxidative induction of the cells with AAPH 40 mM. The data are representative of three independent experiments.

FIG. 11. Effect of DHA concentration in the ARPE-19 cells culture medium on GPx activity. The cells were cultured in the presence of a triglyceride with 70% by weight of DHA in relation to the total fatty acids for three days prior to the experiment. GPx activity was evaluated on the non-induced cellular system or the cellular system induced with 40 mM AAPH. The data are representative of three independent experiments.

FIG. 12. Effect of DHA concentration in the ARPE-19 cells culture medium on SOD activity. The cells were cultured in the presence of a triglyceride with 70% by weight of DHA in relation to the total fatty acids for three days prior to the experiment. SOD activity was evaluated on the non-induced cellular system or the cellular system induced with 40 mM AAPH. The data are representative of three independent experiments.

FIG. 13. Effect of DHA concentration obtained by chemical synthesis (A and C) or enzymatic synthesis (B and D) on the percentage of cellular protection versus oxidative stress in ARPE-19 cells (A and B) or Foreskin cells (C and D).

FIG. 14. Influence of purification degree of the oil obtained by chemical synthesis on the percentage of cellular protection versus oxidative stress induced by DHA in ARPE-19 cells.

FIG. 15. Influence of chemical structure on the percentage of cellular protection versus oxidative stress induced by DHA in ARPE-19 cells.

FIG. 16. Effect of DHA concentration on intracellular concentration of glutation in ARPE-19 cells. Influence of the presence of BSO.

FIG. 17. Influence of glutation de novo synthesis on the percentage of cellular protection versus oxidative stress induced by DHA in ARPE-19 cells.

FIG. 18. Effect of DHA concentration on intracellular concentration of glutation in Foreskin cells. Influence of the presence of BSO.

FIG. 19. Influence of purification degree of the oil obtained by chemical synthesis on the percentage of cellular protection versus oxidative stress induced by EPA in ARPE-19 cells. Comparative study with DHA.

FIG. 20. Effect of EPA concentration on the percentage of cellular protection versus oxidative stress in Foreskin cells. Comparative study with DHA.

FIG. 21. Effect of EPA concentration on intracellular concentration of glutation in Foreskin cells. Influence of the presence of BSO.

FIG. 22 is a comparative bar graphic showing the effect of the DHA percentage in a structured and non-structured triglyceride at different dosages in respect with the percentage of cell protection.

Said FIG. 22 shows the surprising results of the object of the present addition when comparing a non-structured glyceride chemical structure (triglyceride) with the same structure wherein sn-1 and sn-3 positions have been replaced with caprylic acid (structured), both from an enzymatic source with two starting levels in content of DHA of 20 and 70%.

From the figure, it can be observed that at the same concentration, the percentage of protection of the docosahexaenoic acid incorporated into the sn-2 position of a glyceride (structured), in particular, a triglyceride, shows an efficiency which is approximately 3 times higher than that of a glyceride containing non-structured DHA.

In such a FIG. 22, the protection percentage indicates the relationship between the difference in the intracellular concentration of reactive oxygen species of control cells and those treated with DHA in respect with the control cells, both subjected to the same oxidative stress expressed in percentage. In other words, the existence of a protection percentage indicates in the treated cells a significant statistically less intracellular generation of reactive oxygen species in respect with the control.

FIG. 23 is a comparative graphic showing the average length of the telomere in human fibroblasts cultured under oxidative stress with or without DHA incorporated vs. the pass number of cellular populations.

Said FIG. 23 shows the surprising results of the object of the present addition at observing that in presence of DHA under oxidative stress conditions, the telomere shortening index is lower in respect to the control or without DHA.

Figure 1:
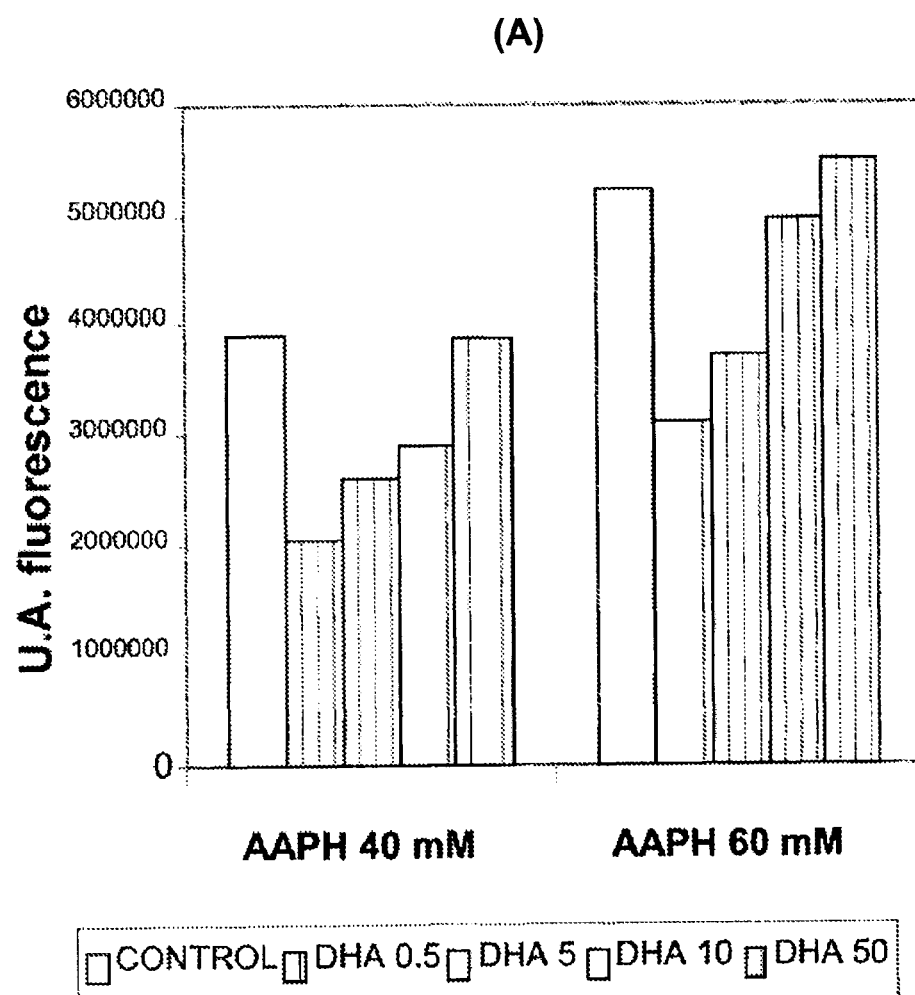
Figure 1:
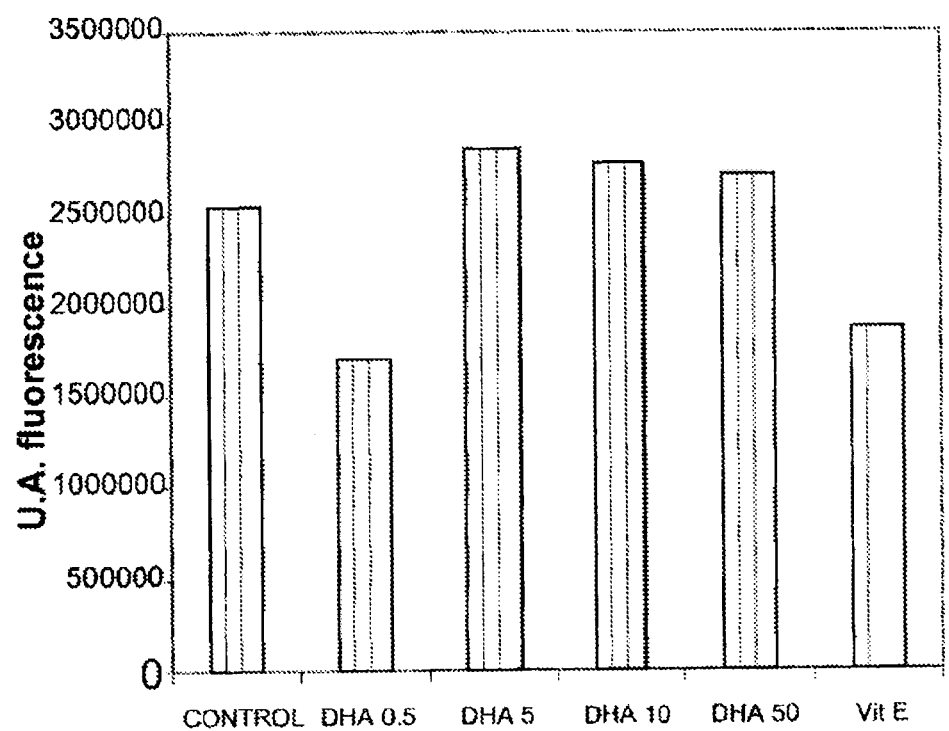

The following examples are included by way of illustrative and non-limitative examples of the invention.

EXAMPLES

Materials and Methods for Evaluating Antioxidant Activity
Cell Cultures

The cellular models used were Foreskin cells (undifferentiated epidermal fibroblasts, CRL-2076) and ARPE-19 cells (retina pigmentary epithelial cells, CRL-2302) obtained from the American Type Culture Collection. The cell cultures were kept in suitable growth conditions of temperature (37° C.), $CO_2$ concentration (5%) and humidity (95%) in an incubator specially designed for this purpose. The ARPE-19 cells were maintained in growth up to confluence of $0.3 \times 10^4$ cells/cm$^2$ in culture flasks with DMEM-F12 medium (Biological Industries) supplemented with 10% bovine foetal serum, penicillin antibiotics (100 U/mL), streptomycin (100 µg/mL) and glutamine (Biological Industries). The CRL-2076 fibroblasts were kept growing in culture flasks in Iscove's modified Dulbecco's medium (Biological Industries) supplemented with 10% bovine foetal serum, penicillin antibiotics (100 U/mL), streptomycin (100 µg/mL) and glutamine (Biological Industries). The cells were transferred for adherence to the substrate 24 h at 37° C. from the 75 ml flasks to 6, 12 or 96-well plates in order to be able to carry out the experiment ($10^6$ cells/mL).

Integration of the DHA into the Cells

DHA-TG was added at various concentrations (0.5-50 µM) starting with the DHA-TG enriched with 20, 50 and 70% (oil density 0.92 g/mL), made by dissolving the oil in ethanol for the stock solution (1:100) and preparing the working solutions in a culture medium prepared with serum. The cells were cultured with supplemented DHA-TG medium for 3 days at 37° C.

Inducing Oxidative Stress

Various inducer cells were used to stress the cells oxidatively:
  a) xanthine/xanthine oxidase system 0.8 mM/$10^{-2}$ U/mL that catalyses the oxidation of hypoxanthine and xanthine to uric acid, with reduction of $O_2$ to $O.^{-2}$ and $H_2O_2$.
  b) 2,2'-azobis-(2-amidinopropane)dihydrochloride (AAPH) 1-100 mM widely used as a hydrophilic initiator of free radicals by inducing lipidic and protein peroxidation. The AAPH oxidises the DNA, the proteins and the lipids through the action of the formed peroxil radicals. It further acts on the endogenous defence system, since it deactivates the key enzyme, the SOD, thereby losing the protective capacity of the CAT and the GPx.

Generation of Reactive Oxygen Species (ROS)

The ROS level was measured in primary cultures of human skin CRL-2076 fibroblasts and in ARPE-19 retinal epithelial cells by employing the fluorimetric technique using dihydrorodamine 123 (DHR123, Molecular Probes) and 2,7-dichlorofluorescein diacetate ($H_2$DCFDA, Molecular Probes) as fluorescent probes in a continuous system measuring every 30 min until 180 minutes. In both cases, this is an unspecific measurement of ROS generation. The fluorescent probes were added to the cells ($1 \times 10^6$ cells/mL) at a final concentration of 10 µM. The fluorescence of the oxidised probes (2,7-dichlorofluorescein and rodamine 123) was measured in a Mithras fluorescence reader at an excitation wavelength of 488 nm and an emission wavelength of 525 nm in function of the time. The fluorescence obtained is modulated with the cellular viability determinations by the MTT spectrophotometric technique outlined below.

Cellular Viability

Cellular viability studies were carried out in order to evaluate the cytotoxic effect of various samples. This method consists of adding the MTT reagent (3-(4,5-dimethylthiazol-2-yl)-2,5-diphenyltetrazoyl bromide, Sigma), soluble in aqueous medium, to the incubation medium. The viable cells metabolise this compound and it is converted into formazan salt. This salt is a colorimetric compound insoluble in aqueous medium, soluble in DMSO and usable for measuring cellular viability. The method consists of adding 20 µl per well of a 7.5 mg/ml (in excess) MTT solution. This is incubated for one hour at 37° C. so that the viable cells metabolise the compound and produce the formazan salt, while the non-viable ones do not. After incubating for one hour the cells are precipitated and 100 µl of DMSO added, which will dissolve the formazan salt. Finally, the absorbance at 550 nm is read on a plate reader. The viability results are expressed as an optical density percentage in relation to the controls, taking the latter to have 100% viability. Cellular viability curves were drawn up on 96-well plates by sowing about 20,000 cells per well (following analysis of the suitable number of cells in function of their growth ratio) with an approximate volume of 200 µl of medium per well. The study of the efficiency of the product is carried out after exposing the cells to the product for 72 h in a sufficiently wide range of concentrations to find the value of $IC_{50}$. The experimental results are adjusted to the Hill equation using the Sigma Plot 8.0 to determine the $IC_{50}$, defined as the DHA concentration necessary to reduce the viability of the culture to 50% in relation to the control.

Determination of Proteins

The determination is based on colorimetric detection and total quantification of the proteins with an optimised dizinconinic acid formulation that allows proteins to be measured in diluted samples in a concentration range of 0.5-20 µg/ml. The method uses a detector for $Cu^{+1}$, which is reduced by the proteins in alkaline medium to $Cu^{+2}$. The purple reaction product is formed by chelation of two molecules of BCA with the cuprous ion. The water-soluble complex absorbs at 562 nm. By means of a calibration curve an equation can be obtained, with the results expressed in µg/mL of proteins. The commercial kit used is the MicroBCA from Pierce (No. 23235).

Direct Analysis of ROS Generation

Measurement of Generation of Lipidic Hydroperoxides

The measurement of malonildialdehyde (MDA) on cell lysates was used as a marker of lipidic peroxidation by UV-Vis spectrophotometry. The MDA and the 4-hydroxyalkenals (HAE) are products derived from the peroxidation of polyunsaturated fatty acids and related esters. Direct measurements of these aldehydes constitutes a convenient index of lipidic peroxidation. A chromogenic reagent (N-methyl-2-phenyl-indole in acetonitrile) which reacts with the MDA at 45° C. was employed, using the commercial lipidic peroxidation kit from Calbiochem (No. 437634). The condensation of one molecule of MDA with two molecules of the chromogenic reagent gives a stable chromophore with maximum absorbance at 586 nm, with the detection limit being 0.1 µM. The induction was carried out for 6 h with 40 mM AAPH and 24 hours of latency. The cells ($10^7$ cells/mL) were lysed by means of cycles of freezing and thawing in liquid $N_2$. The samples were fractionated in order to measure MDA and protein. The results were expressed in µM of MDA/mg of protein.

Measurement of Generation of Superoxide Anion

Direct measurement of the superoxide anion was carried out by means of the chemiluminescence technique on microplate measured by luminol (Calbiochem, No. 574590). Chemiluminescence for detecting the superoxide anion is a technique used due to its potential for gaining access to all the intracellular sites of superoxide generation, due to the high specificity of the reaction with luminol, the minimal intracellular toxicity and the increased sensitivity in relation to other chemical techniques. It is based on the superoxide anion oxidising luminol in a reaction that produces photons of light which are quickly measured on a standard illuminometer. In our tests we used a chemiluminescence reader on microplate from ELISA, MITHRAS and furthermore, given the short half-life of the radical, an enhancer was used to increase the sensitivity of the test and amplify the response. This reagent can be used on living cells, since it is not toxic and does not denature the subcellular system components. The capacity for inhibiting the production of superoxide anion was also investigated using a specific superoxide anion sequestering agent, Tyron (4,5-dihydroxy-1,3-benzene disulphonic acid, Sigma) frequently used for in vitro blocking assays on ROS production, being permeable to the cell membrane and superoxide dismutase (SOD, Sigma) was used as an enzyme blocker, constituting a first-line enzyme in the endogenous antioxidant defence. The chemiluminescence measurement in the cells submitted to the AAPH oxidative stress inducing treatment was analysed every 60 seconds for a total time of 4100 seconds, at a frequency of 120 sec/cycle. The results were expressed in UA of chemiluminescence/mg protein.

Determining Antioxidant Enzyme Activity

Measuring Glutation Peroxidase (GPx) Activity

GPx catalyses the reduction of hydroperoxides to reduced glutation, the function being to protect the cell from oxidative damage. It uses glutation as last electron donor to regenerate the reduced form of selenocysteine. The indirect measurement of GPx is obtained by coupled reaction with glutation reductase. The oxidated glutation (GSSG) produced by the reaction with the hydroperoxides by action of the GPx is recycled to its reduced state by the glutation reductase using NADPH as coenzyme. Oxidation from NADPH to $NADP^+$ is accompanied by reduction of its absorbance at 340 nm. The rate of reduction of the absorbance at 340 nm is directly proportional to the GPx activity of the sample. The ELISA microplate spectrophotometric kit from Cayman (No. 703102) was used for detecting the GPx in cell lysates of primary cultures. The cells were cultured by adherence to the substrate for 24 h at 37° C. The cell lysate was obtained by sonication in Tris 50 mM pH 7.5, EDTA 5 mM and DTT 1 mM. The activity of the GPx is obtained by determining the change of $A_{340}$ nm/min ($\Delta A_{340}$, expressed as nanomoles NADPH/min/mg of protein from the sample.

Measuring the Superoxide Dismutase Activity (SOD)

This chemiluminescence methodology is based on the analysis of SOD activity in the supernatant cellular in relation to a positive control of SOD (Calbiochem No. 574590). The presence of SOD in the xanthine oxidase-xanthine-luminol system leads to a reduction of the chemiluminescence produced as a reduction of dismutation of the superoxide anion proportional to the SOD activity. The analysis is carried out on a MITHRAS illuminometer at intervals of 50 msec up to a final reaction time of 520 sec.

The superoxide dismutase activity (SOD) in cellular lysates by means of the reaction using tetrazolium salts for detecting superoxide radicals generated by xanthine oxidase/hypoxanthine system has been also determined. An spectrophotometric method is used on a microplate for measuring the 3 types of SOD (Cu—Zn-SOD; Mn-SOD and Fe-SOD), that is cytosolic and mitochondrial). One unit of SOD is defined as the quantity of enzyme required for dismuting 50% of the generated superoxide anion. In order to detect SOD in cellular lysates from primary cultures a Cayman kit (N. 706002) was used following the protocol optimized by the manufacturer. The dynamic range of the assay is 0.025-0.25 SOD units/ml.

Determination of Intracellular Endogenous Antioxidant Concentration

Measuring the Reduced Glutation Intracellular Concentration (GSH)

Direct kinetic assay for measuring reduced glutation (GSH) in cellular lysates. Glutation can be found inside the cells mainly in the reduced form (90-95% of total glutation), being the main antioxidant in tissues. Its role is detoxifying xenobiotics and removing hydroperoxides so as to keep the cellular redox state. The technique employed measures the total glutation (GSSG+GSH) in a biological sample (cellular lysate) previously deproteinized with sulphosalicylic acid (Sigma-Aldrich CS0260 kit). GSH causes a continuous reduction from 5,5'-dithiobis(2-nitrobenzoic) acid (DTNB) to 5-thio(2-nitrobenzoic acid (TNB) and the GSSG formed is recycled by glutation reductase and NADPH. TNB is spectrophometrically measured at 412 nm. Buthionine sulfoximine (BSO) specifically inhibiting gamma-glutamylcysteine synthetase was used as a synthesis inhibitor.

Evaluation of the Anti-Oxidant Activity of DHA in a Human Skin Model

In this in vitro assay Foreskin cells (undifferentiated epidermal fibroblasts, ATCC CRL-2076) were used as cellular model, being a suitable cellular type due to their good in vitro response to various oxidant inducers, in addition to being a primary culture with normal nutritional requirements and culture conditions, thus constituting a good in vitro model extrapolable to the in vivo response, for a potential cosmetic application of the DHA.

Results

The conditions were laid down initially to achieve an active cellular model under all study conditions. This means that the results obtained refer to metabolically active cells. Prior studies had already shown that in Foreskin cells concentrations of less than 1000 μM of DHA did not affect cellular viability in studies at 3 days. Neither was cellular viability affected for the studies of oxidative stress with the xanthine/xanthine oxidase system or with AAPH. It has also been shown that the incorporation of DHA up to a concentration of 50 μM in a culture of Foreskin cells for 3 days does not significantly increase the cellular oxidative level measured as cellular fluorescence associated with two probes, dihydrorodamine (DHR 123) and 2,7-dichlorofluorescein ($H_2DCFDA$), more specific for superoxide anion and for the detection of hydroperoxides, respectively. Once these conditions had been established, the general antioxidant capacity of the DHA incorporated into the membrane of the Foreskin cells was evaluated against oxidative stress induced by xanthine/xanthine oxidase or by AAPH.

When inducing a moderate oxidative stress with 40 mM AAPH and using DHR123 as ROS detector, the DHA shows an inhibiting effect on the generation of the reactive oxygen species, both at the concentration of 0.5 μM (59% protection) and at 5 μM (33% protection), showing a lower effect at 10 μM (26% protection) or no effect at 50 μM of DHA (FIG. 1A). When the cells are submitted to severe induction with 60 mM AAPH, the DHA shows a protective effect against the generation of ROS, both at 0.5 μM concentration (40% protection) and 5 μM (29% protection), but losing it at higher concentrations of DHA (FIG. 1A).

We might also note the protection that 0.5 μM DHA exercises against the oxidative stress induced by the xanthine/xanthine oxidase (FIG. 1B), which shows a sequestering effect on the oxygen reactive species, both superoxide anion and hydroperoxides generated in the oxidative process. Comparing the antioxidant capacity in relation to a lipophilic antioxidant such as vitamin E (FIG. 1B), we observe that they exercise similar protection kinetics (with DHA inhibiting cellular oxidation by 33.46% and vitamin E by 30%).

Figure 2:
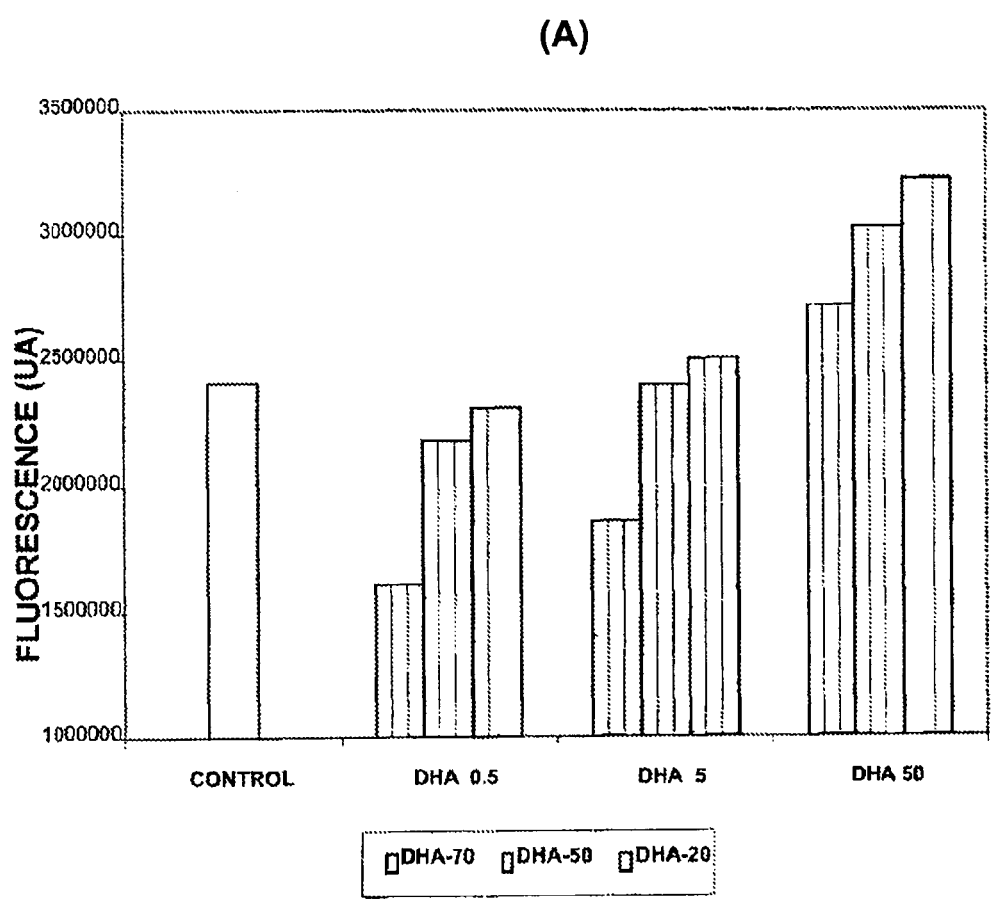
Figure 2:
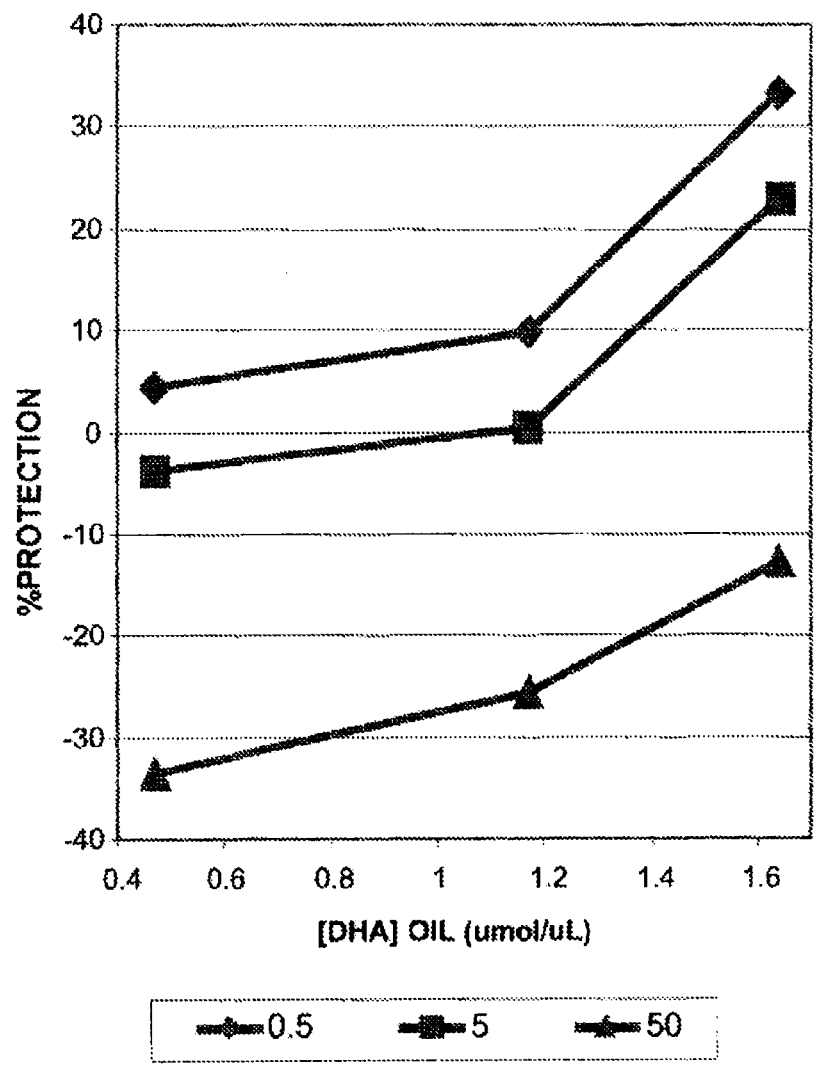

The protection kinetic response of the DHA always presents a maximum antioxidant effect between 60-120 minutes after carrying out the induction, thus denoting a saturation in the hydroperoxides and superoxide anion sequestering capacity of the DHA. The antioxidant behaviour is critically dose-dependent, since increasing the concentration thereof leads to a loss of ROS sequestering capacity, with the 0.5 μM concentration having the most effective antioxidant capacity. In this regard, another critical parameter in terms of optimising the efficiency of the system is the proportion of DMA in relation to total fatty acids. As shown in FIG. 2, at identical concentrations of triglyceride, a reduction of the proportion of DHA to 50 or 20% drastically reduces the cellular antioxidant capacity, and it reverts to being pro-oxidant at low or moderate concentrations. These results appear to indicate that the cellular antioxidant effect of the DHA does not depend exclusively on the concentration thereof, but also it is a decisive factor its molecular localisation, in this case its distribution in the structure of the triglyceride.

Figure 3:
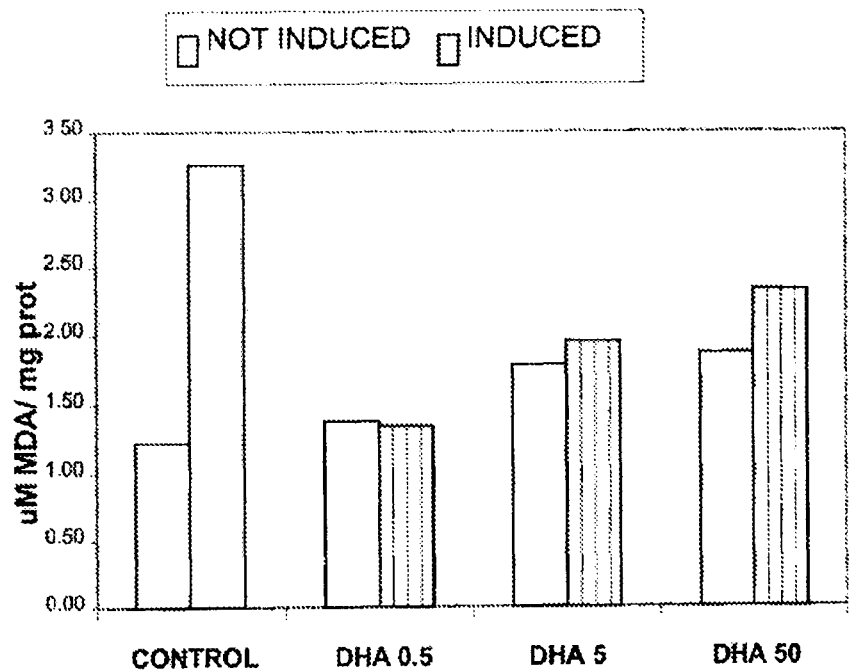

As regards specific inhibition of ROS production, we analysed the generation of lipidic peroxides (TBARS) and of superoxide anions. The results obtained showed that the cells treated with AAPH generated a higher concentration of substances reactive to thiobarbituric acid (TBARS) when compared with the non-induced cells, expressed as μM of MDA/mg of proteins (FIG. 3). As expected, incorporation of DHA into the membrane of the Foreskin cells slightly increased the basal cellular lipidic peroxidation in dose-dependent form (0.5, 5 and μM) (FIG. 3). In the cells submitted to oxidative induction with 40 mM AAPH, the DHA presents an antioxidant activity protecting the fibroblasts from generating membrane hydrolipidic peroxides, its action being of the inverse concentration-dependent type. The protection with DHA was 87% for 0.5 μM DHA, 85% for 5 μM and 48% for 50 μM DHA-TG (FIG. 3).

Figure 4:
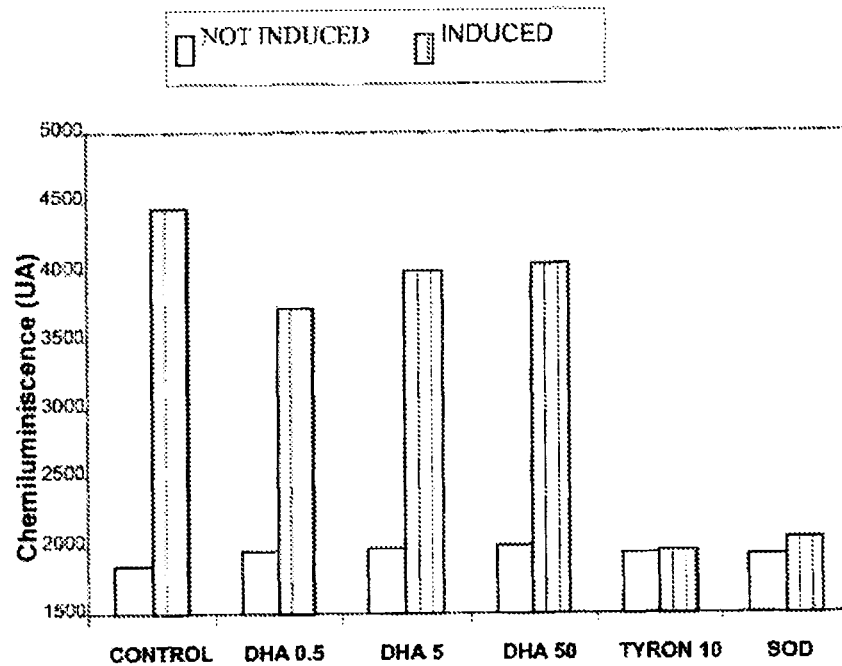

Generation of the superoxide anion was then analysed. Foreskin cells submitted to an oxidative stress with 40 mM AAPH generated a superoxide anion production 2.5 times greater than the non-induced cells, which maintained a constant superoxide anion level (FIG. 4). In the absence of oxidative induction the cells with integrated DHA do not show a higher level of intercellular superoxide anion in relation to control (FIG. 4). Under oxidative stress conditions (FIG. 4) the DHA inhibits generation of the superoxide anion by 16.5% at a concentration of 0.5 μM, by 10% at a concentration of 5 μM and by 9% at a concentration of 50 μM. The specificity of the method was confirmed by the addition of Tyron (4,5-dihydroxy-1,3-benzene disulphonic acid, a compound which is permeable to the cellular membrane that operates as a highly specific sequestering agent of intracellular superoxide anion) or of extracellular SOD (first-line enzyme blocker in the endogenous antioxidant defence via dismutation of the intracellular superoxide anion). The production of the superoxide anion in cells stressed with AAPH, with or without DHA previously integrated, in the presence of exogenous SOD or of Tyron, was totally inhibited and achieved basal values (FIG. 4).

Figure 5A:
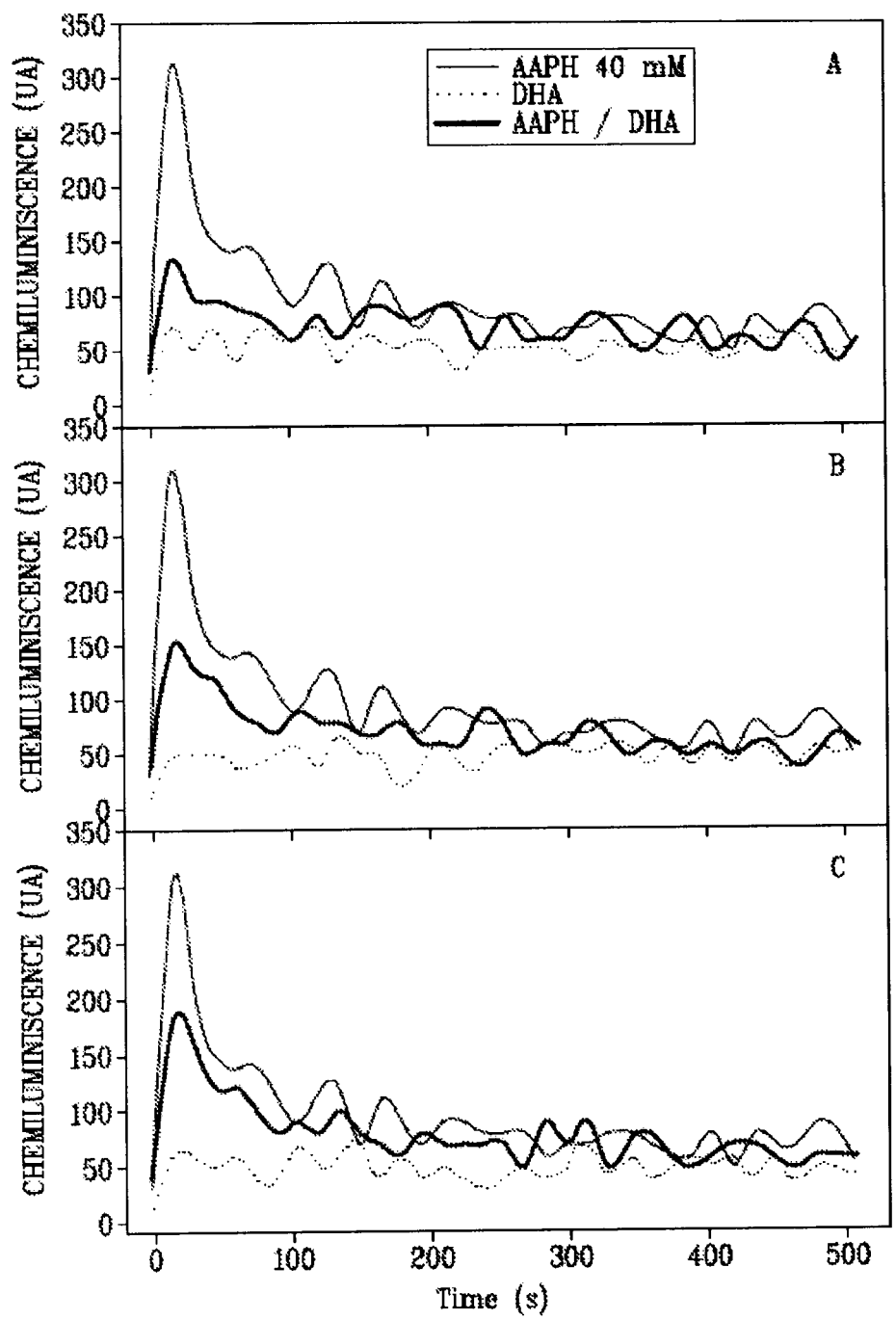
Figure 5B:
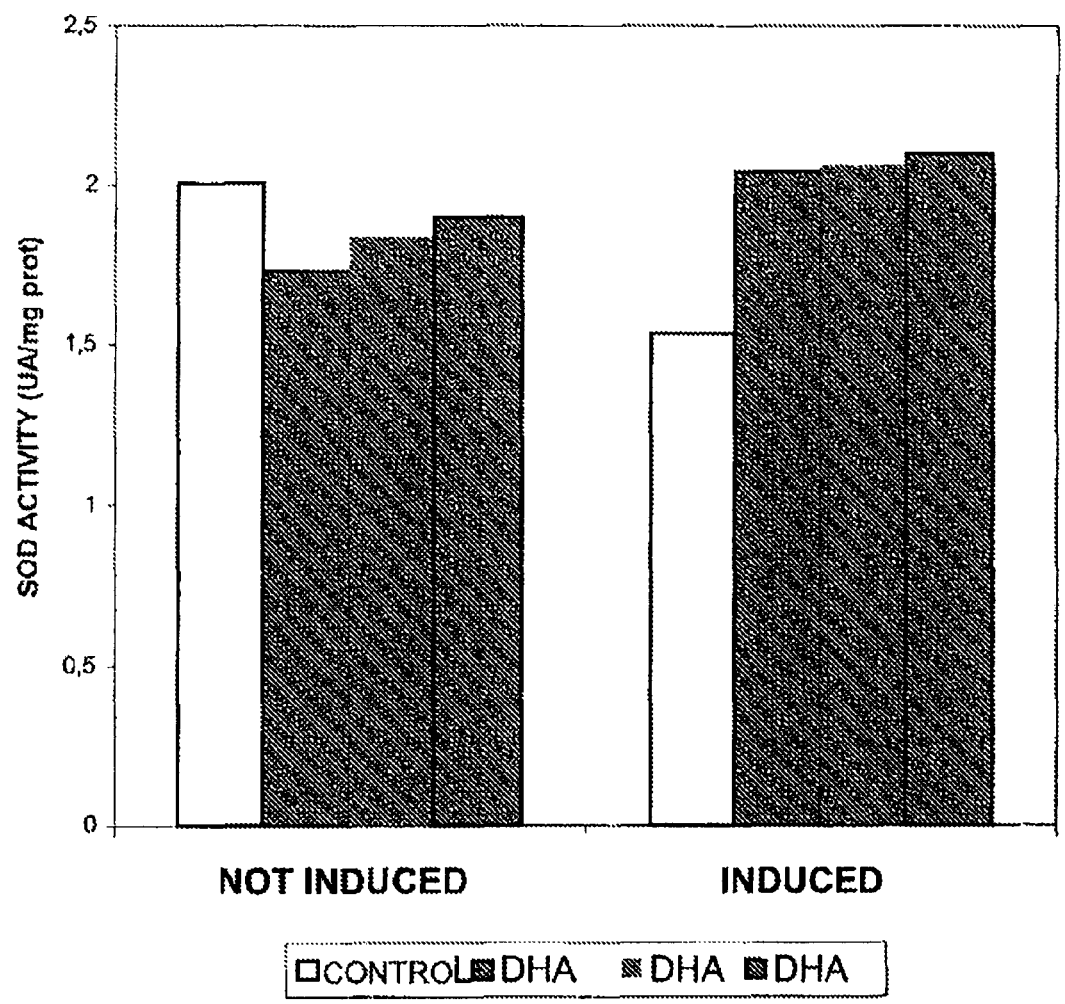
Figure 6:
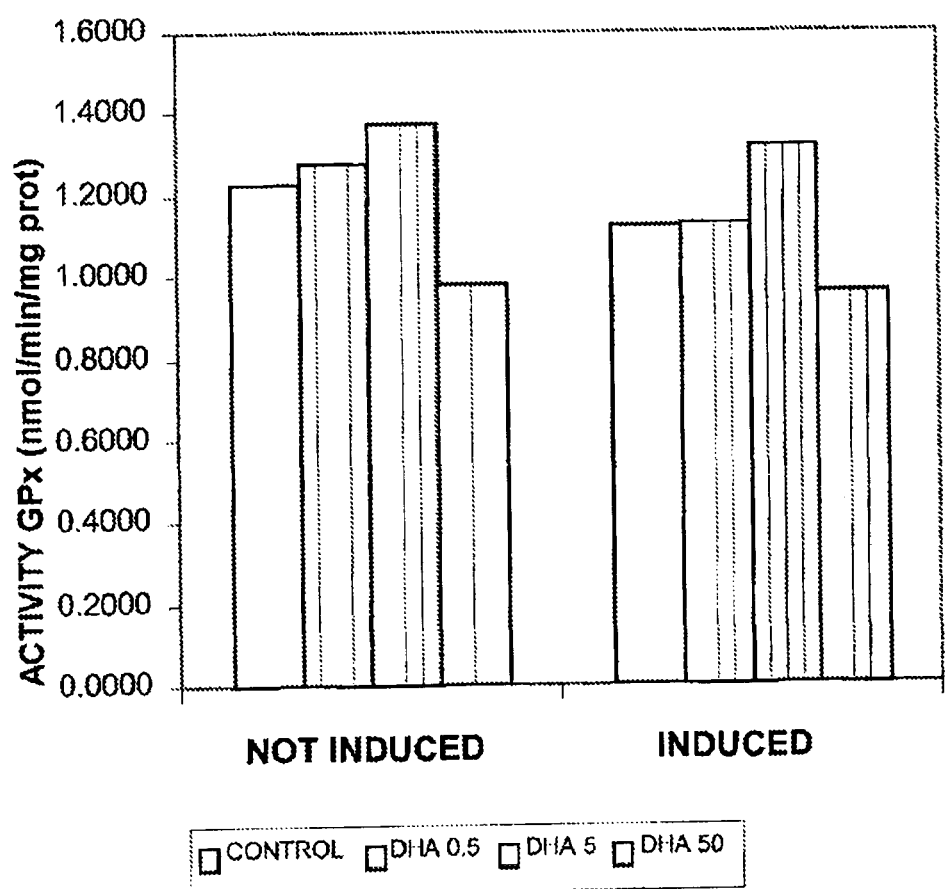

Finally, we analysed if the DHA underwent its antioxidant activity by modifying the activity of the first-line cellular antioxidant enzymes. The activity of the SOD and of the GPx in Foreskin cells with or without integrated DHA was analysed. In the first case, the xanthine/xanthine oxidase system was used as instantaneous generator of superoxide anions (total measuring time 520 sec., measuring every 50 msec.). The results obtained showed a good oxidative induction with rapid kinetics, with direct observation of dismutation and non-production of superoxide anion. The maximum chemiluminescence achieved after 15 seconds from oxidative induction was interpreted as an indirect and qualitative measurement of SOD activity (FIG. 5A). Without DHA integrated, values of 310 U.A. chemiluminescence/$10^6$ cells were achieved, falling to 150 U.A. chemiluminescence/$10^6$ cells in a system pre-incubated with DHA 0.5 μM (52% antioxidant protection) (FIG. 5A). The antioxidant efficiency was maintained at 52% and 42% protection in cells treated with 5 and 50 μM of DHA, respectively (FIG. 5A). Furthermore, knowing that AAPH oxidises the DNA, the proteins and the lipids by diffusion of the generated peroxil radicals, the DHA as antioxidant may prevent deactivation of the SOD entrusted with dismutation of the superoxide anion, maintaining in the cell the endogenous antioxidant defence of the catalase and the glutation peroxidase. This aspect is confirmed in FIG. 5B, wherein SOD activity is shown not to be increased in basal state with DHA being present (−10/−15%), but loss of SOD activity inherent to the oxidative stress process is inhibited with DHA being present keeping or even increasing SOD activity (10/20%). As for GPx activity (FIG. 6), this is found to be increased in cellular basal state at modest concentrations of DHA (up to 17% at 5 µM), but falls off at high concentrations (−20% at 50 µM). This behaviour is maintained intact in an oxidative stress state (FIG. 6). These results suggest that the DHA collaborates with the endogenous antioxidant defence system as relates to dismutation of the superoxide anion by generating SOD over the entire range of concentrations tested, and is also capable of controlling the generation of hydroperoxides at moderate concentrations, since it increases GPx activity.

Evaluation of the Antioxidant Activity of DHA in a Retina Cellular Model

In this in vitro study the cellular model was based on ARPE-19 cells (pigmentary retinal epithelial cells, ATCC CRL-2302), being a suitable cellular type due to their good in vitro response to various oxidant inducers, as well as being a primary culture with normal nutritional requirements and culture conditions. It also constitutes a good ocular model, since it keeps the biological and functional properties of the retinal pigmentary epithelial cells.

Results

The assay carried out with this cellular line is similar to that described for the Foreskin cells in the preceding section. The basic requirements were the same in relation to keeping cellular viability under all working conditions (effect of the DHA, of oxidative stress). Neither did incorporation of DHA at the doses analysed involved any significant alteration in the basal cellular oxidative state.

Figure 7:
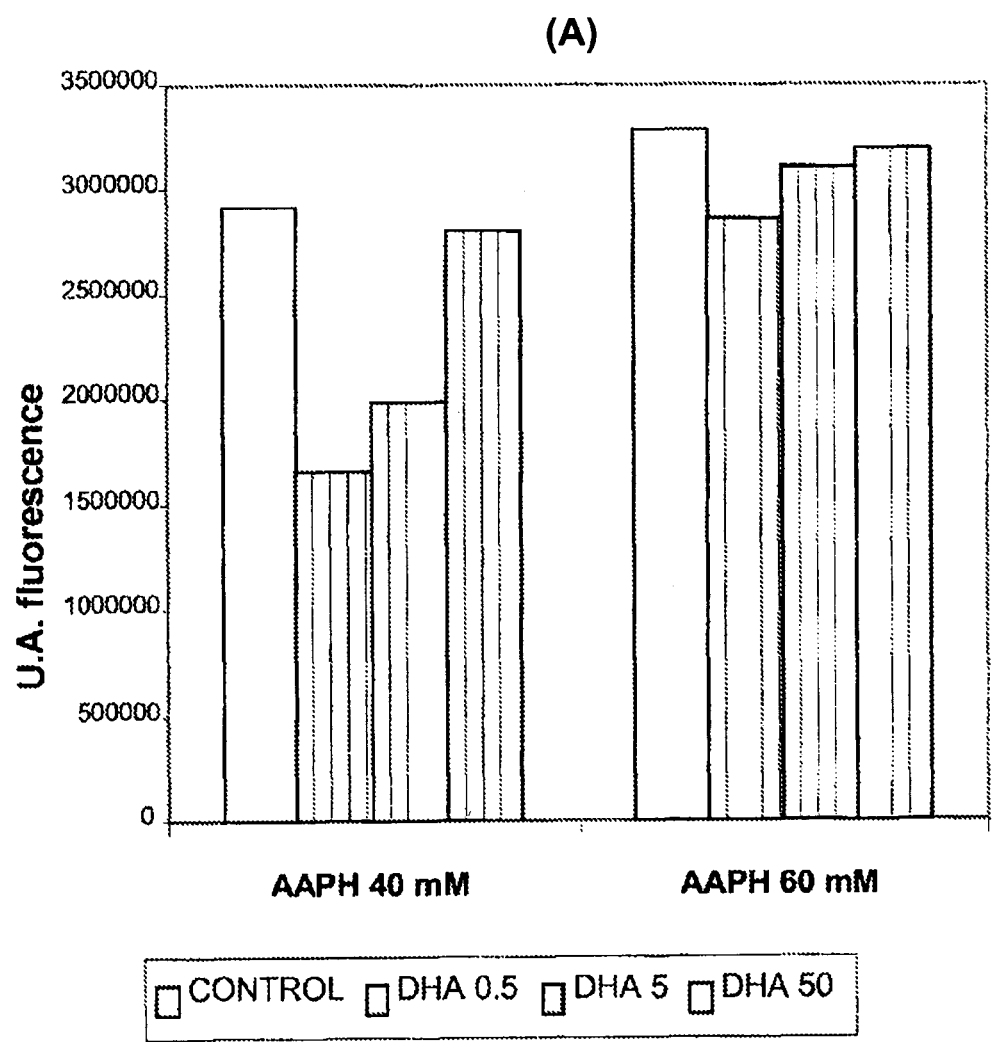
Figure 7:
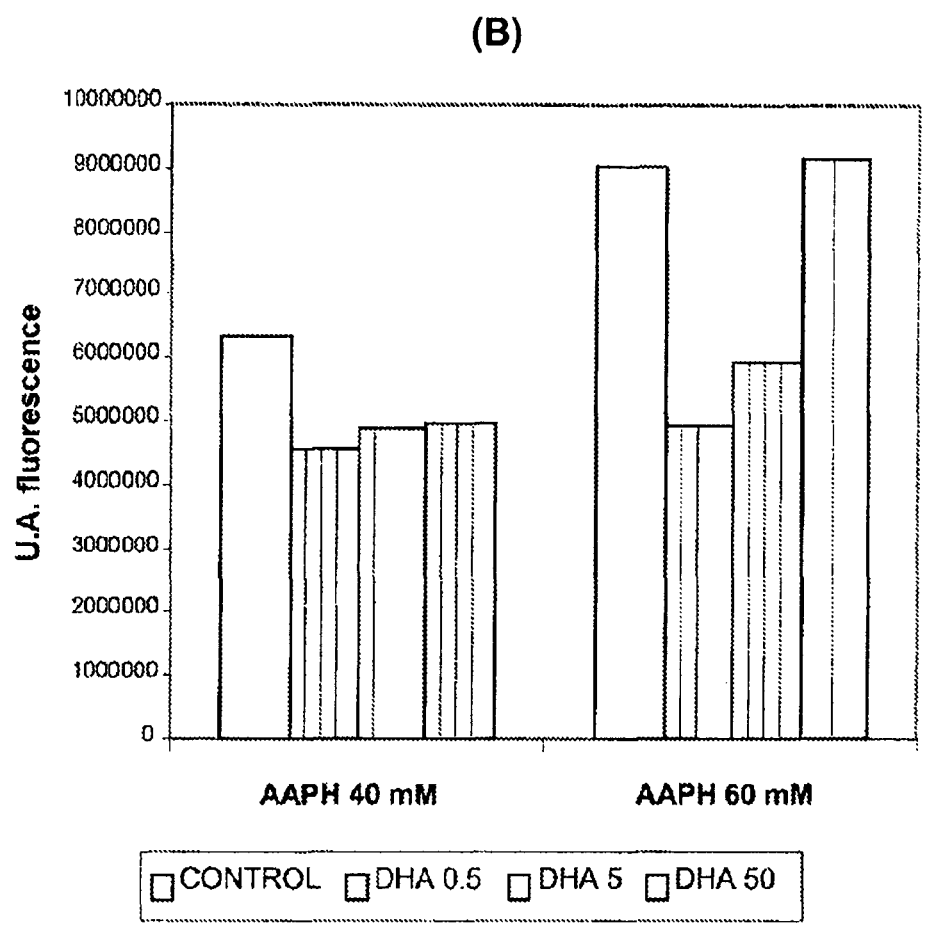

On inducing a moderate oxidative stress with 40 mM AAPH and using DHR123 as ROS detector, the DHA shows an inhibiting effect on the generation of the reactive oxygen species, at the concentrations of 0.5 µM (43% protection) and 5 µM (32% protection), but with a lower effect at 50 µM (4% protection) of DHA (FIG. 7A). When the cells are submitted to severe induction with 60 mM AAPH, the DHA shows a protective effect against ROS generation, at the 0.5 µM concentration (13% protection) and lower at higher concentrations of DHA (FIG. 7A). These results are similar to those obtained with the Foreskin cells, although one notable differential effect is the lower protection observed against a severe oxidative induction. By using for the ROS detection, the CDCFDA more specific to peroxides, it is also revealed the protection that the DHA exercises against the oxidative stress induced by AAPH (FIG. 7B).

Figure 8:
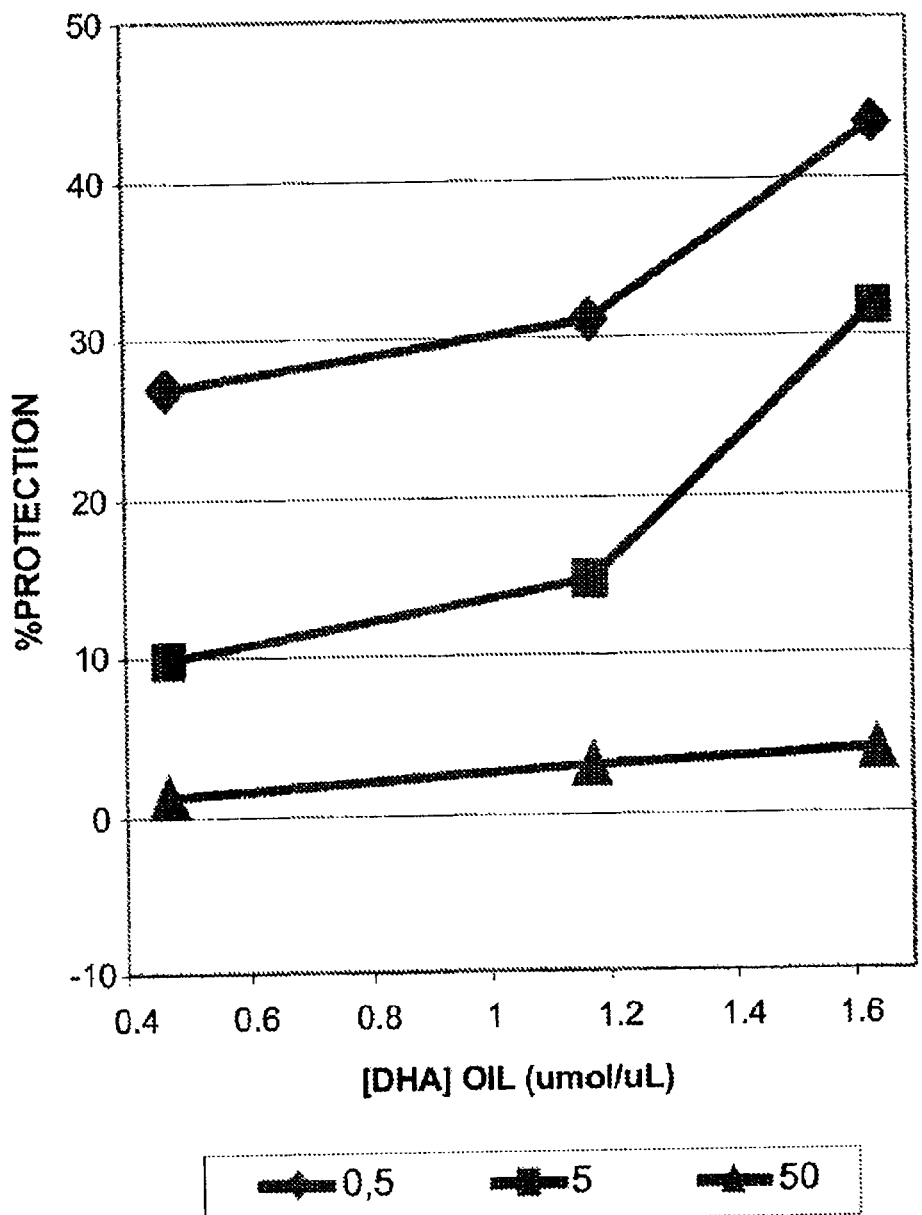
Figure 8:
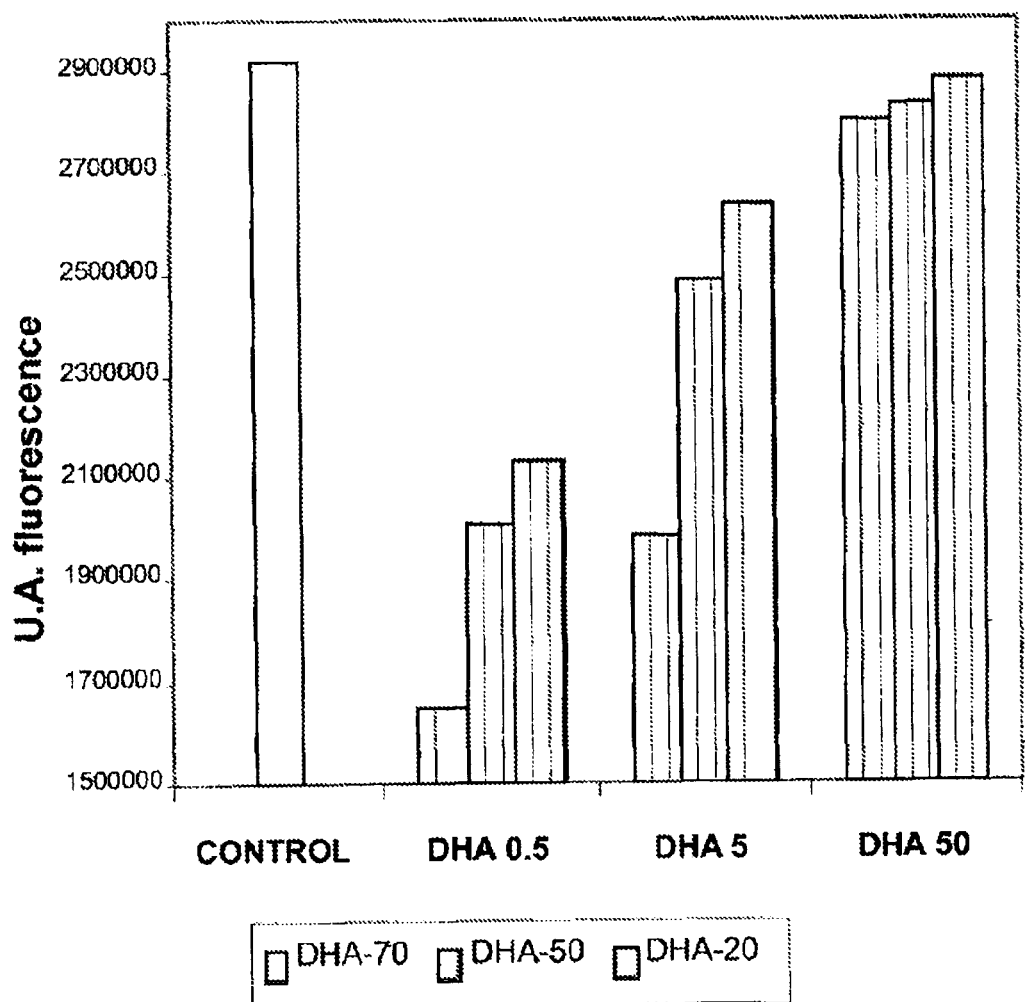

The protection kinetics of the DHA also always presents a maximum antioxidant effect 60-120 minutes after carrying out the induction, denoting a saturation in the DHA's hydroperoxides and superoxide anion sequestering capacity. Quantitatively, the antioxidant capacity is critically dose-dependent, since when DHA concentration is increased there is a loss of ROS sequestering capacity, with the 0.5 µM concentration being the most effective in its antioxidant capacity (FIGS. 7A and 7B). In this respect, another critical parameter in terms of optimising the efficiency of the system is the ratio of DHA to total fatty acids. Reducing the proportion of DHA in relation to total fatty acids from 70% to 50-20% significantly and non-proportionally reduces its cellular antioxidant capacity at the optimum concentrations (0.5-5 µM), rendering it equal to the high concentrations (FIGS. 8A and 8B), though unlike to the Foreskin cells at no proportion does the DHA become pro-oxidant. These results confirm that the cellular antioxidant effect of the DHA does not depend exclusively on its concentration, but also a decisive factor is its molecular localisation, in this case its distribution in the structure of the triglyceride.

Figure 9:
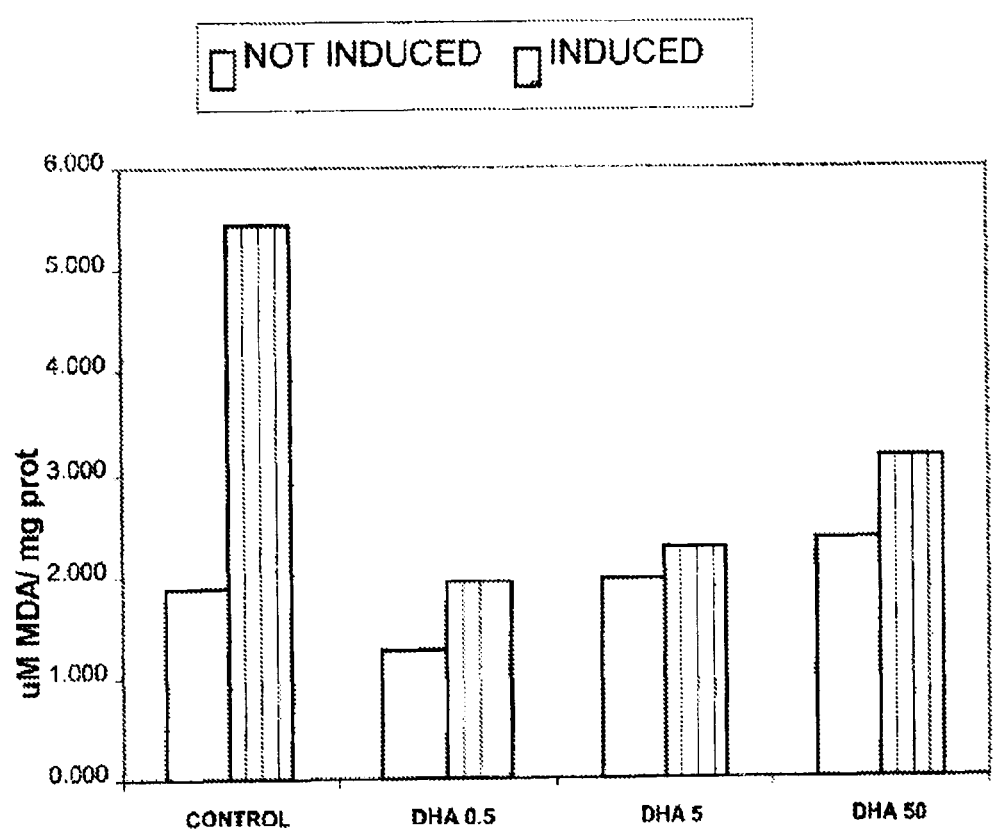
Figure 10:
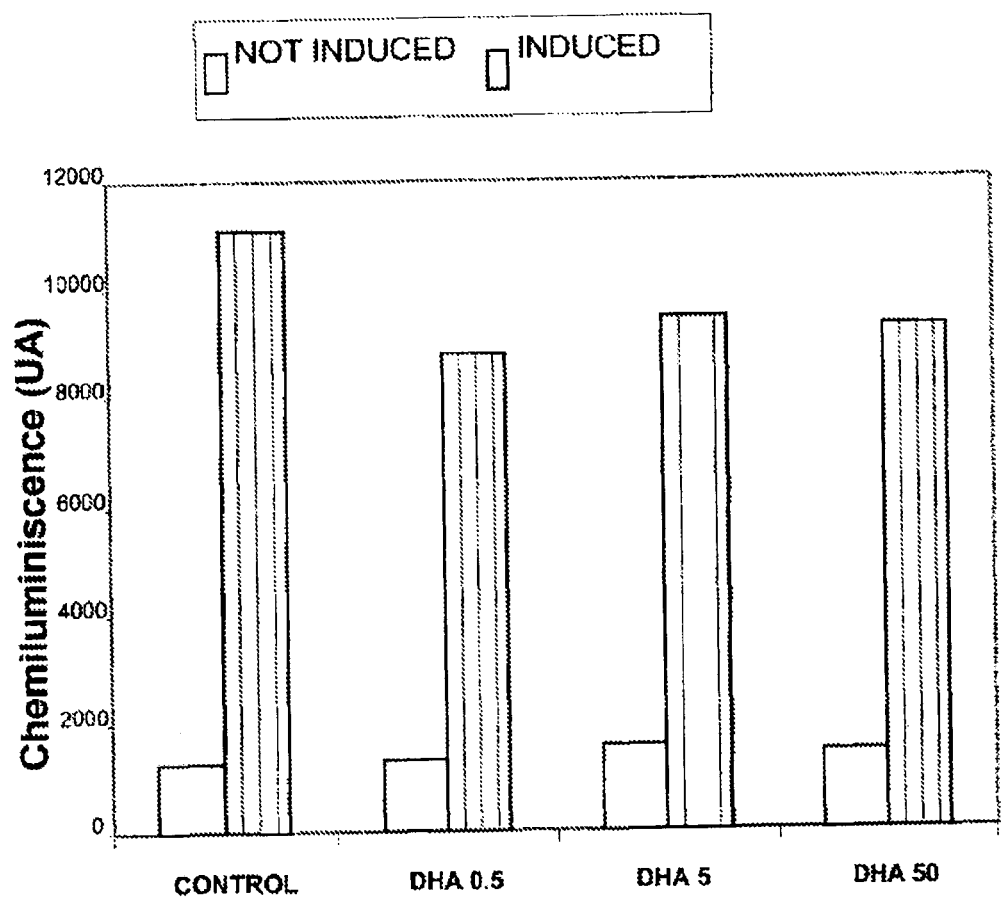

As regards specific inhibition of ROS production, the generation of lipidic peroxides (TBARS) (FIG. 9) and of superoxide anions (FIG. 10) were analysed. The results obtained are very similar to those obtained with the Foreskin cells. The cells treated with AAPH generate a higher concentration of substances reactive to thiobarbituric acid (TBARS) and of superoxide anions in relation to the non-induced cells. The incorporation of DHA into the membrane of the ARPE-19 cells slightly and dose-dependently (0.5, 5 and 50 µM) increases the cellular basal lipidic peroxidation, though in the cells submitted to oxidative induction, the DHA presents a cellular antioxidant activity inhibiting them from generating membrane lipidic hydroperoxides in an inverse ratio to their concentration. The protection with DHA was 64% for 0.5 µM DHA, 58% for 5 µM and 42% for 50 µM DHA (FIG. 9). Generation of the superoxide anion was then analysed. In the absence of oxidative induction, the cells with integrated DHA do not present a higher level of intracellular superoxide anion in relation to the control (FIG. 10A). An oxidative stress with 40 mM AAPH generates a superoxide anion production that is partially inhibited by the DHA (20-16% at concentrations of 0.5-50 µM). This inhibition is in concordance with SOD activity with DHA being present (FIG. 10B). SOD activity is not found to be increased in basal state with DHA being present (−10/15%), but as in Foreskin cells, loss of SOD activity inherent to the oxidative stress process is inhibited with DHA being present keeping basal SOD activity.

Figure 11:
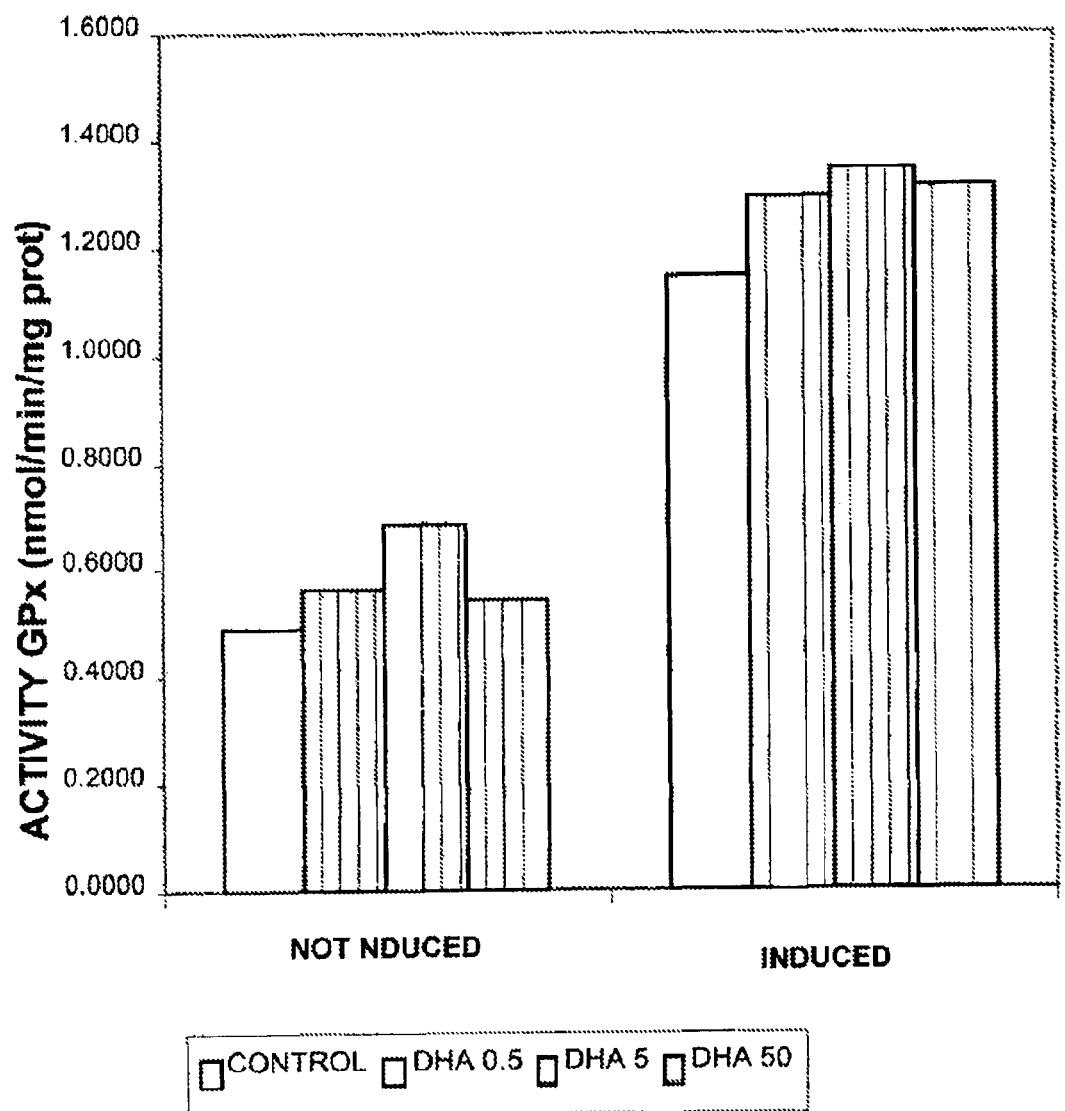
Figure 12:
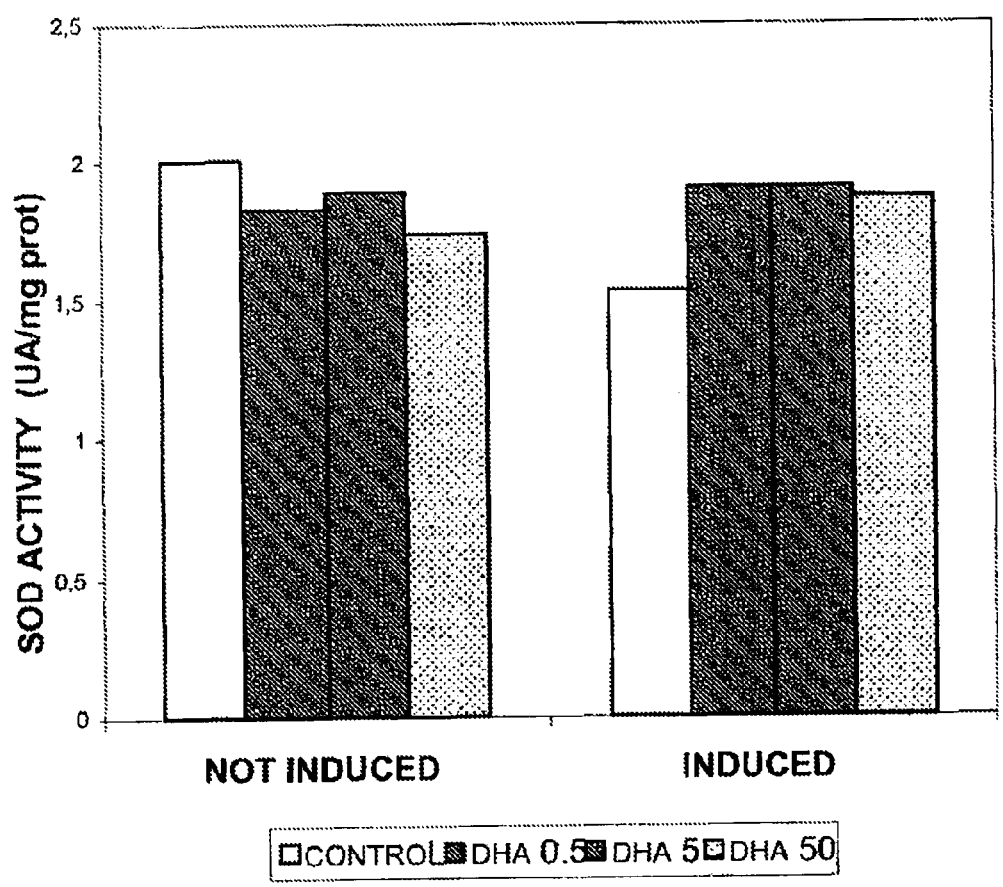

Finally, an analysis was carried out to find whether the DHA altered the activity of the GPx enzyme as first-line cellular antioxidant (FIG. 11). The GPx activity is increased in cellular basal state at all the concentrations of DHA tested (12-40%), and this behaviour is maintained intact in oxidative induction state, which also presents a 2.5 times higher GPx activity (FIG. 11). As in the case of the Foreskin cells, these results suggest that the DHA exercises part of its antioxidant effect by modulating the activity of the endogenous cellular enzyme system antioxidant defence.

Influence of Synthesis Method in the Antioxidant Activity of DHA Incorporated into a Triglyceride In the present in vitro assay, ARPE-19 cells (retina pigmentary epithelial cells, ATCC CRL-2302) and Foreskin cells (undifferentiated epidermal fibroblasts, ATCC CRL-2076) were used as cellular model, being suitable cellular lines due to their good in vitro response to various oxidant inducers. Tuna oil triglycerides (DHA20%-TG, 20% molar in DHA) or oil derivatives enriched with 50 or 70% molar in DHA (DHA50%-TG and DHA70%-TG) obtained by chemical methods (CHEM) or enymatic methodes (ENZ) were used an active ingredient.

Results

Figure 13:
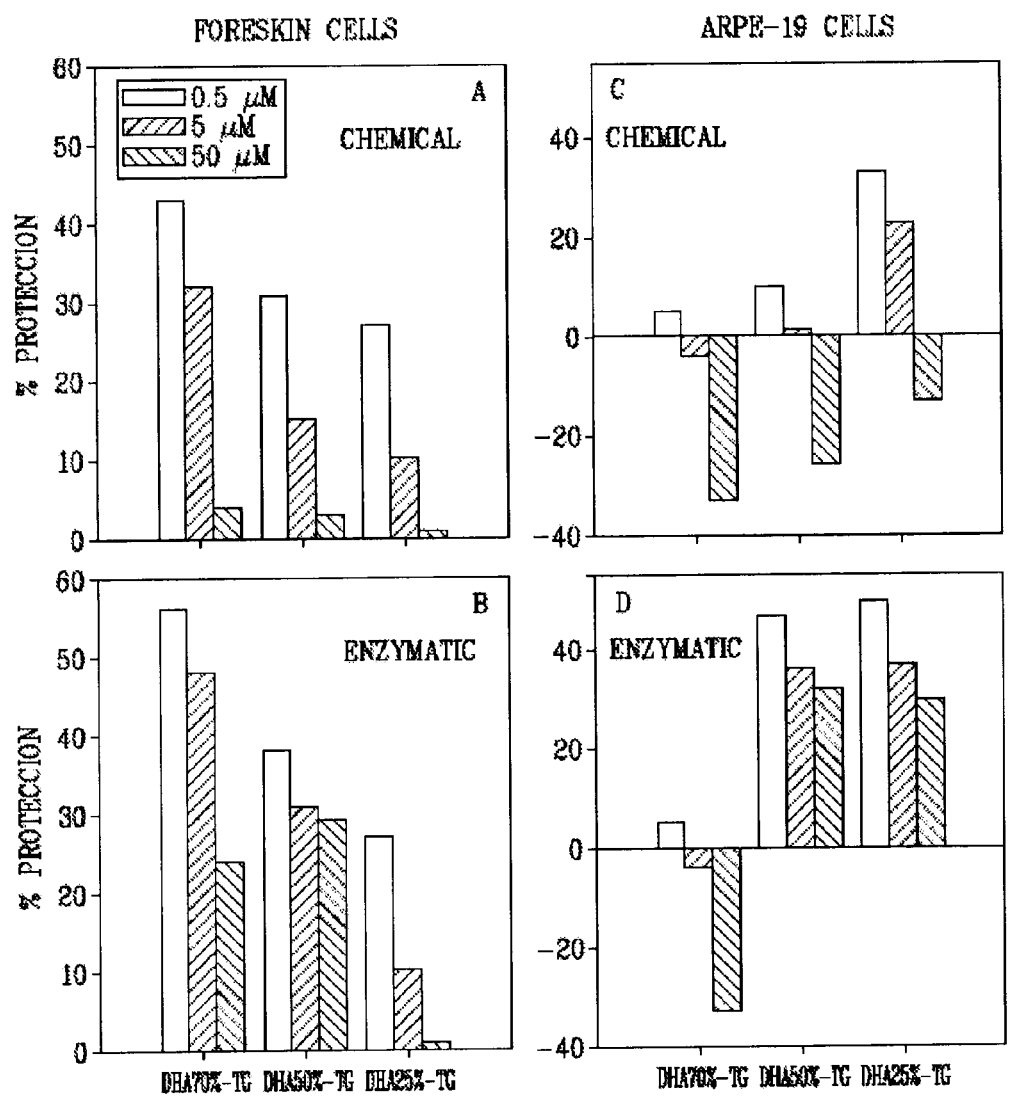
Figure 14:
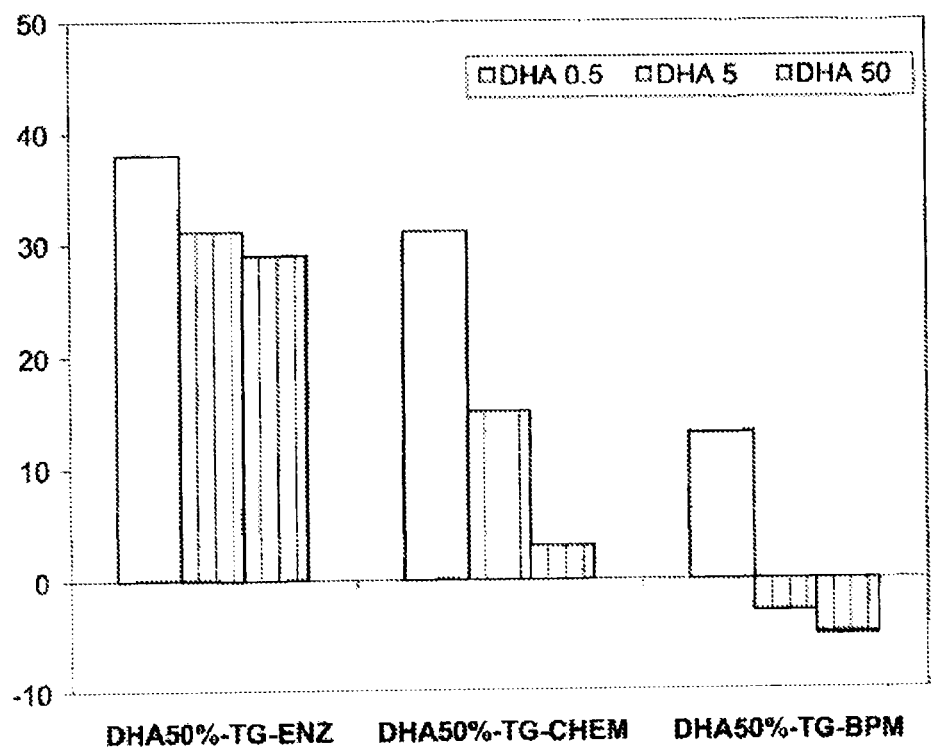
Figure 15:
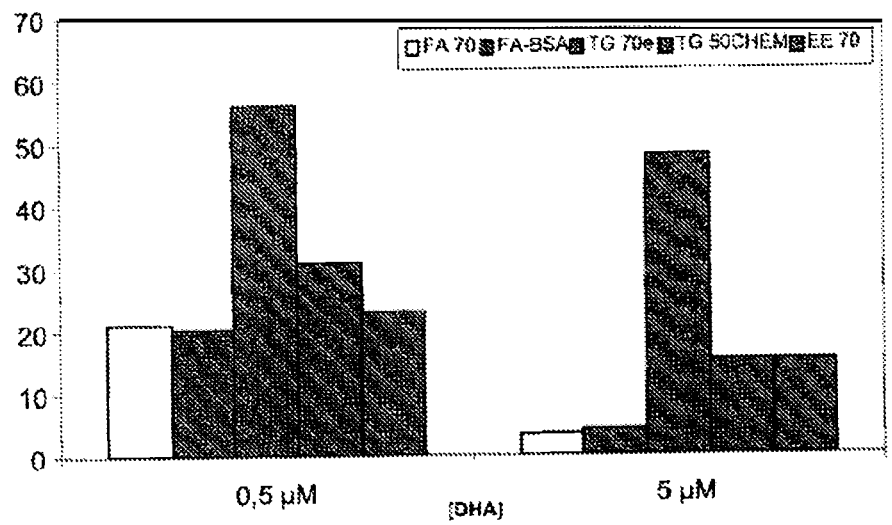

When inducing a moderate oxidative stress with 40 mM AAPH in ARPE-19 cells and using DHR123 or $H_2$DCFDA as ROS intracellular detectors, the natural DHA (DHA20%-TG) and that incorporated into a chemically obtained triglyceride (DHA50%-TG-CHEM and DHA70%-TG-CHEM) shows an inhibitory effect in the generation of the reactive oxygen species, both 0.5 µM and 5 µM concentration, showing a lower effect at 50 µM (FIG. 13A). This effect depends on the content of DHA, being DHA70%-TG-CHEM>DHA50%-TG-CHEM>DHA20%-TG. At the same concentrations (0.5, 5 and 50 µM), enzimatically obtained oils show a higher activity at all DHA contents (DHA70%-TG-ENZ and DHA50%-TG-ENZ) (FIG. 13B). In a similar study with Foreskin cells the results were even more surprising. The pro-oxidative activity shown with DHA70%-TG-CHEM and DHA50%-TG-CHEM at high dose (FIG. 13C) becomes antioxidative at all concentrations with oils with enzymatic origin (DHA70%-TG-ENZ and DHA50%-TG-ENZ) (FIG. 13D). The removal of intrinsic polymers of oils obtained chemically by means of chromatographic methods (DHA70%-Tg- BPM) causes a decrease even greater of antioxidative activity in aRPE-19 cells, becoming prooxidative at high concentrations (5 and 50 µM) (FIG. 14). The antioxidative activity of DHA incorporated into a triglyceride obtained by enzymatic synthesis is also higher (at least twice) than that shown by Dha incorporated inton other chemical structures such as ethyl esters, free fatty acid o fatty acid linked to serum albumin (FIG. 15).

Figure 16:
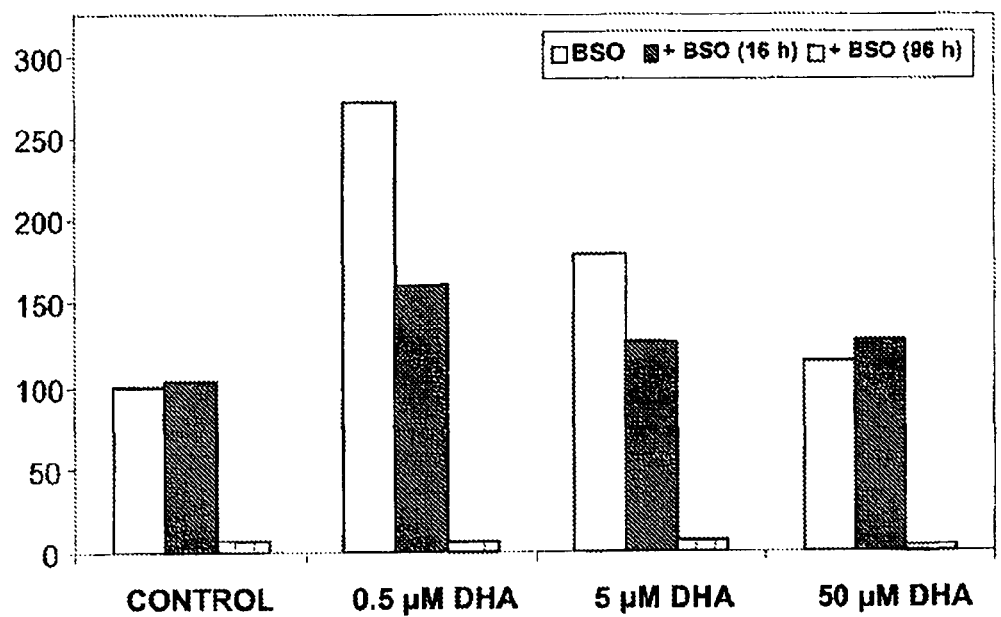
Figure 17:
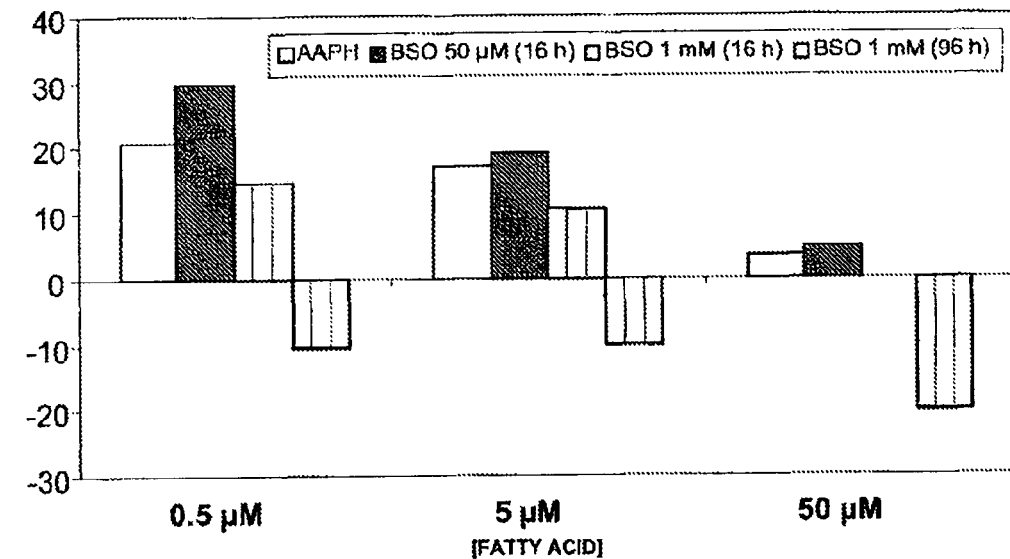
Figure 18:
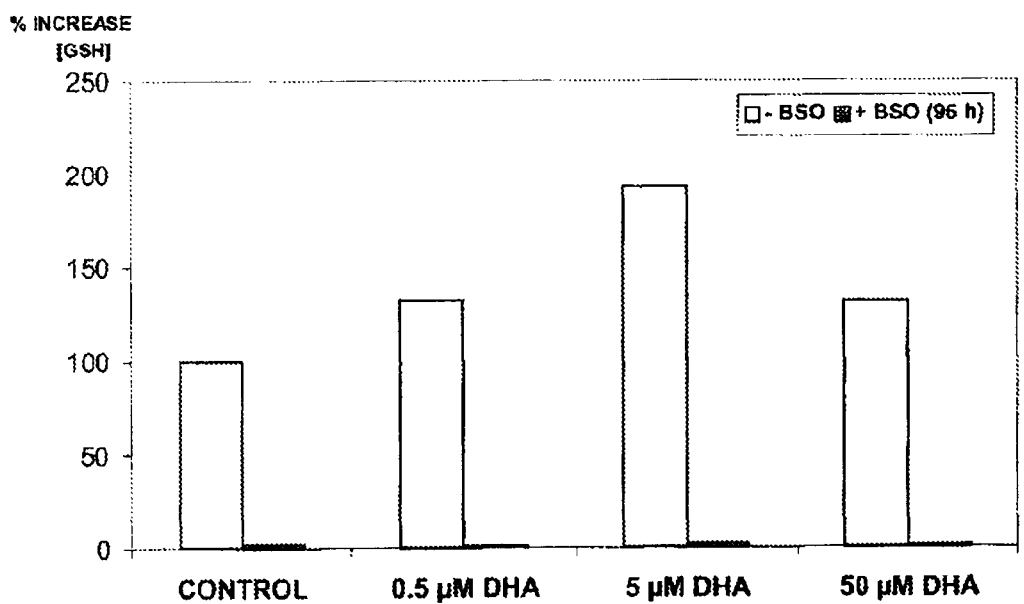

The cellular antioxidative activity shown with the incorporation of DHA is related to all the aspects previously considered such as maintaining SOD and GPX enzymatic activities, but also to an increase in glutation intracellular concentration (GSH). In ARPE-19 cells (FIG. 16), DHA induces an increase in the GSH intracellular concentration directly related to GSH de novo synthesis since the addition of BSO (specific inhibitor of GSH synthesis) eliminates the protective effect of DHA (FIG. 17) in a direct relation with a decrease in the GSH intracellular concentration (FIG. 15). A similar behaviour is shown for Foreskin cells (FIG. 18).

Figure 19:
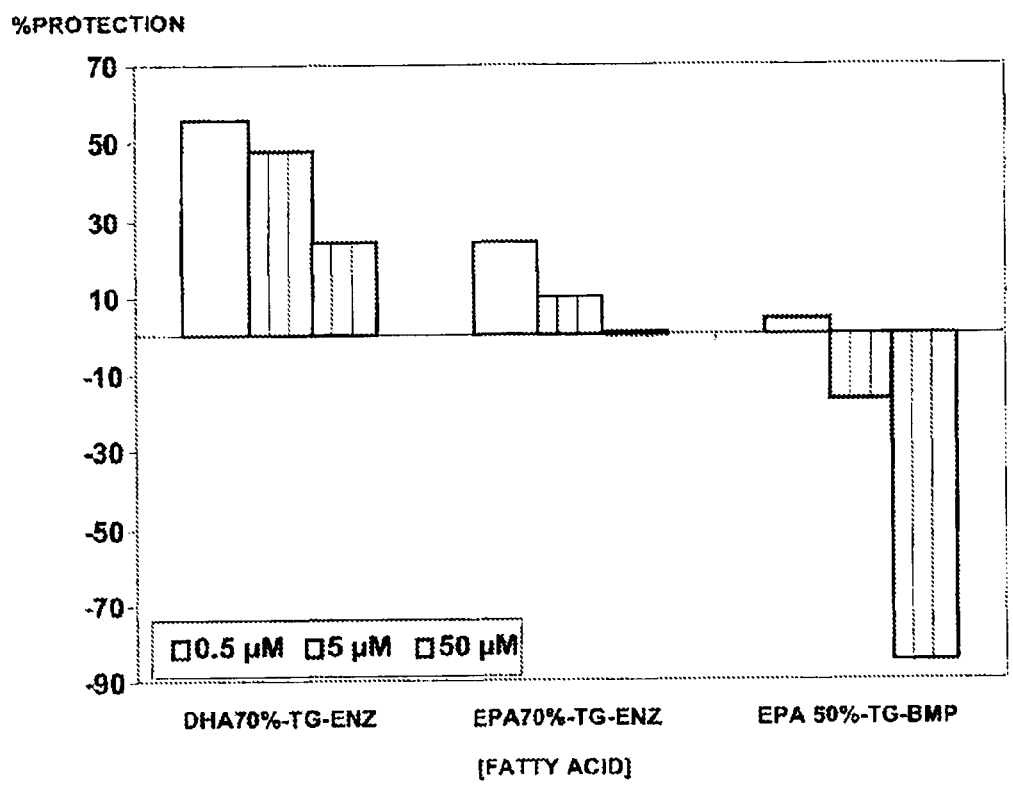
Figure 20:
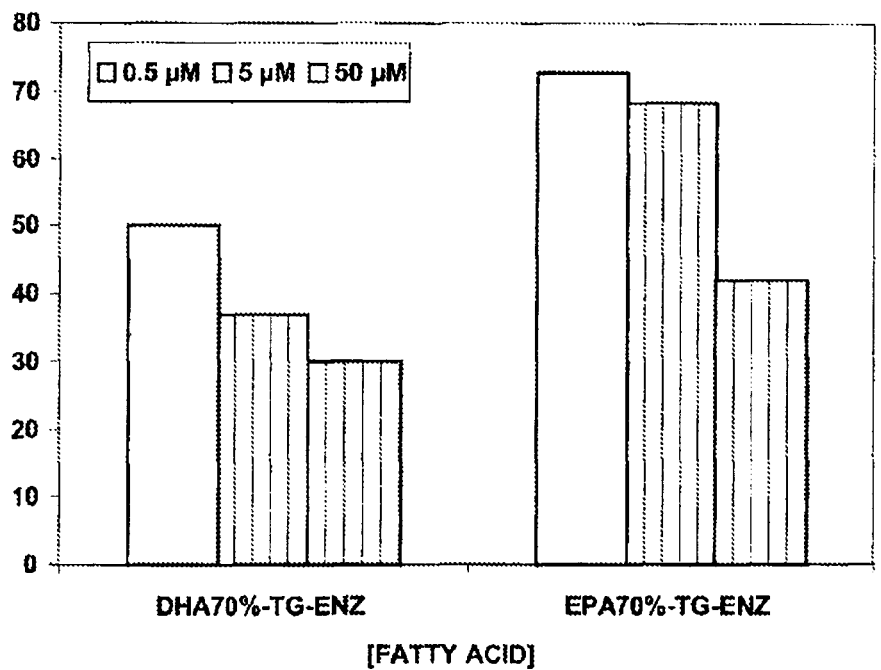
Figure 21:
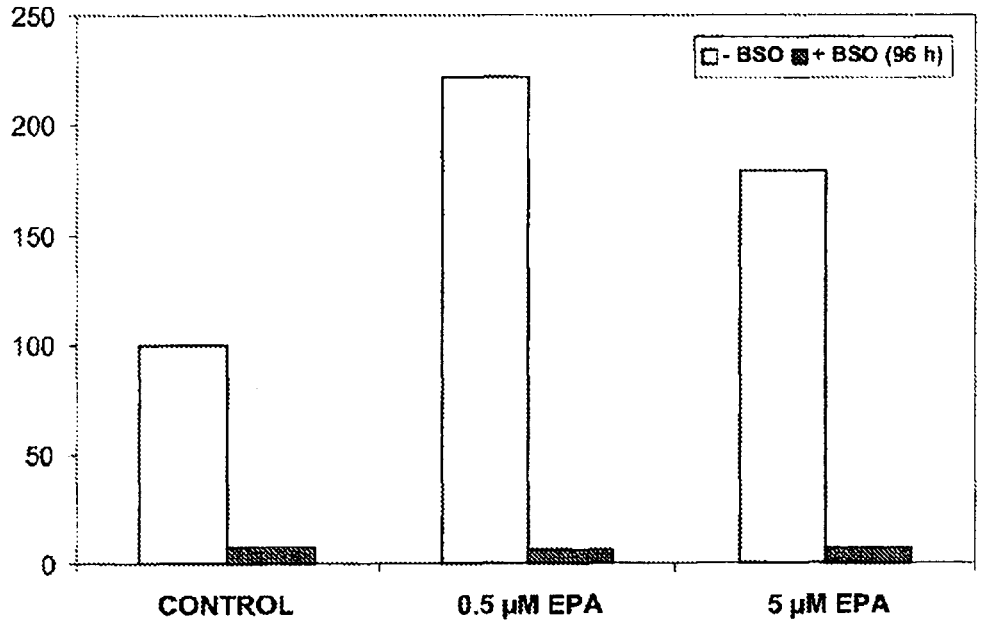

The improvement obtained in the antioxidative activity of DHA by an enzymatic synthesis is also applicable to another omega-3 fatty acid such as eicosapentaenoic acid (EPA). In a study with ARPE-19 cells, EPA obtained enzimatically (EPA70%-TG-ENZ) are shown to have an antioxidative activity, though very lower to that observed with DHA (DHA70%-TG-ENZ), whereas EPA obtained chemically and free of polymers (EPA-70%-TG-BPM) is shown to be very prooxidative (FIG. 19). Furthermore, EPA (EPA70%-Tg-ENZ) obtained enzimatically shows in Foreskin cells a remarkable antioxidative activity even higher than that for DHA (DHA70%-TG-ENZ) (FIG. 20), related to, just like for DHA, the increase of GSH intracellular concentration (FIG. 21).

Evaluating the Antioxidant Activity of the DHA Incorporated into a Structured Triglyceride in a Retina Cellular Model In this in vitro assay ARPE-19 cells (retina pigmentary epithelial cells, ATCC CRL-2302) were used as cellular model, being a suitable cellular type due to their good in vitro response to various oxidant inducers, in addition to being a primary culture with normal nutritional requirements and culture conditions. Furthermore, it is a good ocular model since it keeps the biological and functional properties of the retina pigmentary epithelial cells. As an active ingredient there have been used structured triglycerides derived from tuna oil (DHA20%-TG, 20% molar in DHA) or oil enriched with 70% DHA (DHA70%-TG, 70% molar in DHA), wherein through enzymatic methods the fatty acids in sn-1 and sn-3 positions have been replaced with octanoic acid. In these new compounds, the molar content of DHA is 7% in the DHA20%-TG and 22% in DHA70%-TG.

Figure 22:
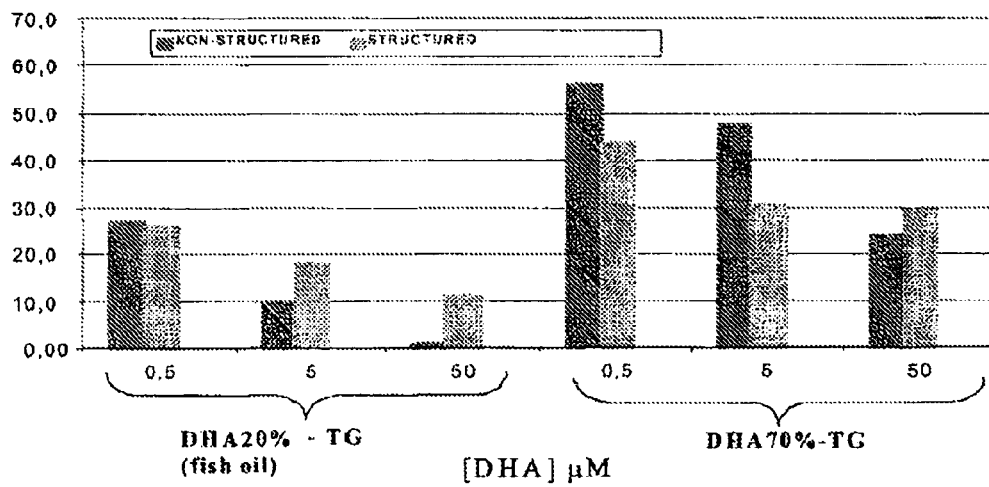

Results (See FIG. 22)

When inducing a moderate oxidative stress with 40 mM AAPH and using DHR123 as ROS detector, the DHA incorporated into a normal triglyceride (DHA20%-TG and DHA70%-TG) shows an inhibitory effect in the generation of the reactive oxygen species, both 0.5 µM and 5 µM concentration, showing a lower effect at 50 µM (FIG. 22). This effect depends on the content of DHA, being DHA70%-TG>DHA20%-TG. At the same concentrations, the structured oils, with a real DHA concentration 2-3 times lower, show the same activity (for 0.5 µM concentration) or higher (for 5 µM and 50 µM concentrations) in the case of DHA20%-TG. In the case of DHA70%-TG, the efficacy of the structured triglyceride is slightly lower than optimum concentrations (0.5 µM and 5 µM), but the behaviour at high concentrations is inverted (50 µM) showing in general a more stable and less dose-dependent behaviour.

Evaluating the DHA Activity as a Protective Agent of the Length of a Telomere Associated to the Age in a Human Skin Model In this in vitro assay Foreskin cells (undifferentiated epidermal fibroblasts, ATCC CRL-2076) were used as cellular model, being a suitable cellular type due to their good in vitro response to various oxidant inducers, in addition to being a primary culture with normal nutritional requirements and culture conditions, thus constituting a good in vitro model extrapolable to the in vivo response, for a potential cosmetic application of the DHA.

Methodology

Cell Cultures

The cellular models used were Foreskin cells (undifferentiated epidermal fibroblasts, CRL-2076) obtained from the American Type Culture Collection. The cell cultures were kept in suitable growth conditions of temperature (37° C.), $CO_2$ concentration (5%) and humidity (95%) in an incubator specially designed for this purpose. The CRL-2076 fibroblasts were kept growing in culture flasks in Iscove's modified Dulbecco's medium (Biological Industries) supplemented with 10% bovine foetal serum, penicillin antibiotics (100 U/mL), streptomycin (100 µg/mL) and glutamine (Biological Industries).

Integration of the DHA into the Cells

Enzymatically synthesized DHA-TG 70% was added at a 0.5 µM concentration, made by dissolving the oil in ethanol for the stock solution (1:100) and preparing the working solutions in a culture medium prepared with serum. The cells were cultured with supplemented DHA-TG medium for 3 days at 37° C.

Induction of Oxidative Stress 2,2'-azobis-(2-amidinopropane)dihydrochloride (AAPH) was used to stress the cells oxidatively at a concentration of 40 mM, widely used as a hydrophilic initiator of free radicals by inducing lipidic and protein peroxidation. The AAPH oxidises the DNA, the proteins and the lipids through the action of the formed peroxil radicals. It further acts on the endogenous defence system, since it deactivates the key enzyme, the SOD, thereby losing the protective capacity of the CAT and the GPx.

Measurement of the Length of the Telomere

The telomeric regions constituted by high repetitive DNA can be evaluated by in situ hibridation techniques. The in situ hibridation method with fluorescence (FISH) using complementary probes to the telomeric sequences allowed to detect the presence or absence of telomeres, as well as quantify the telomeres per cell or per chromosomic group. The method called flow FISH uses flow citometry in combination with the FISH technique using a pan-telomeric PNA (peptide nucleic acid) as a probe and allows to measure, using the fluorescence intensities, the average telomeric lengths at the chromosome ends in individual cells. For our purpose, the fluoresce intensity of PAN labelled with chromosomes at metaphase. The results are expressed as telomere fluorescence unit (TFU) corresponding each TFU to 1 kb of repetitive telomeres.

Results

Figure 23:
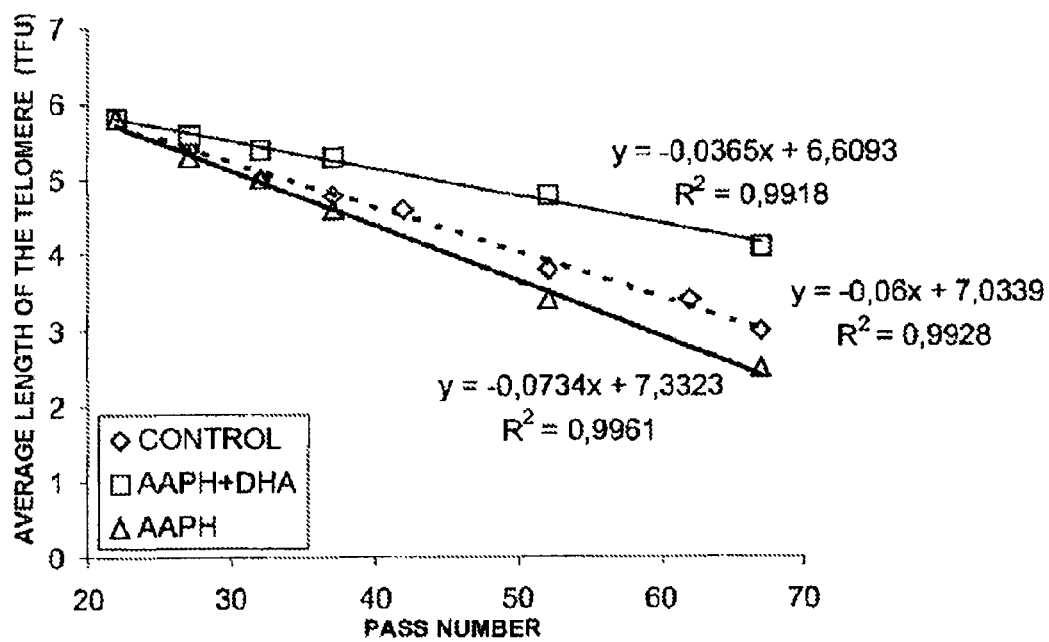
Figure 24:
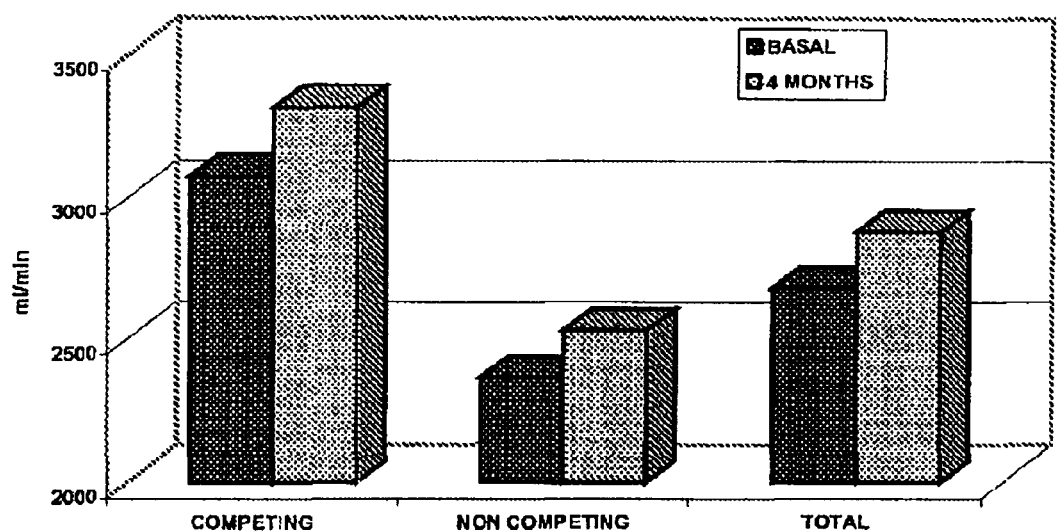
FIG. 24 is a graphic representing the absolute oxygen consumption in the "ventilatory threshold 2" (UV2) for competing, non-competing and all cyclists at basal level and after 4 months taking DHA.
Figure 25:
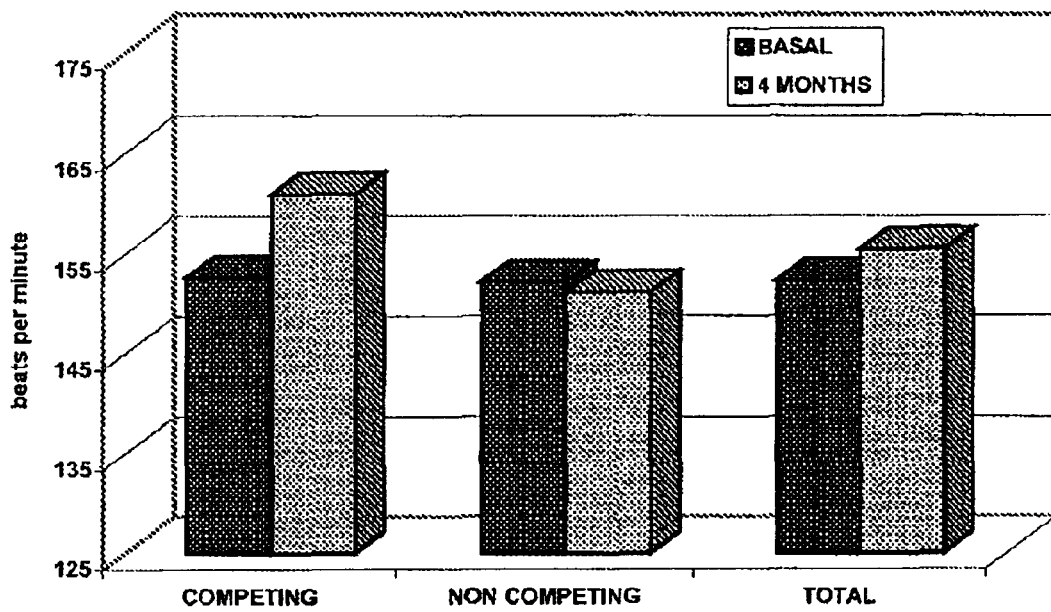
FIG. 25 is a graphic representing the cardiac frequency in UV2 for competing, non-competing and all cyclists at basal level and after 4 months taking DHA.
Figure 26:
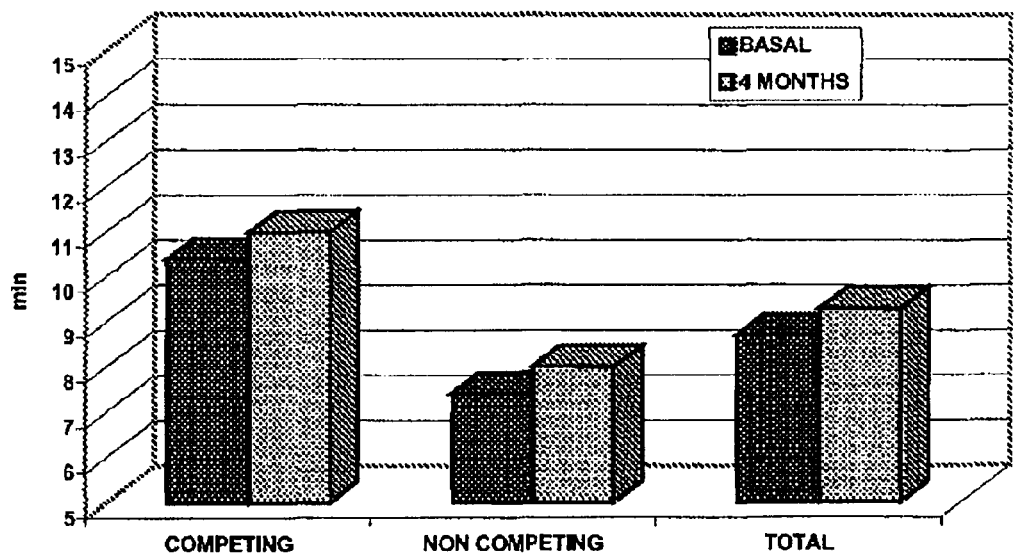
FIG. 26 is a graphic representing the time needed to reach the UV2 for competing, non-competing and all cyclists at basal level and after 4 months taking DHA.
Figure 27:
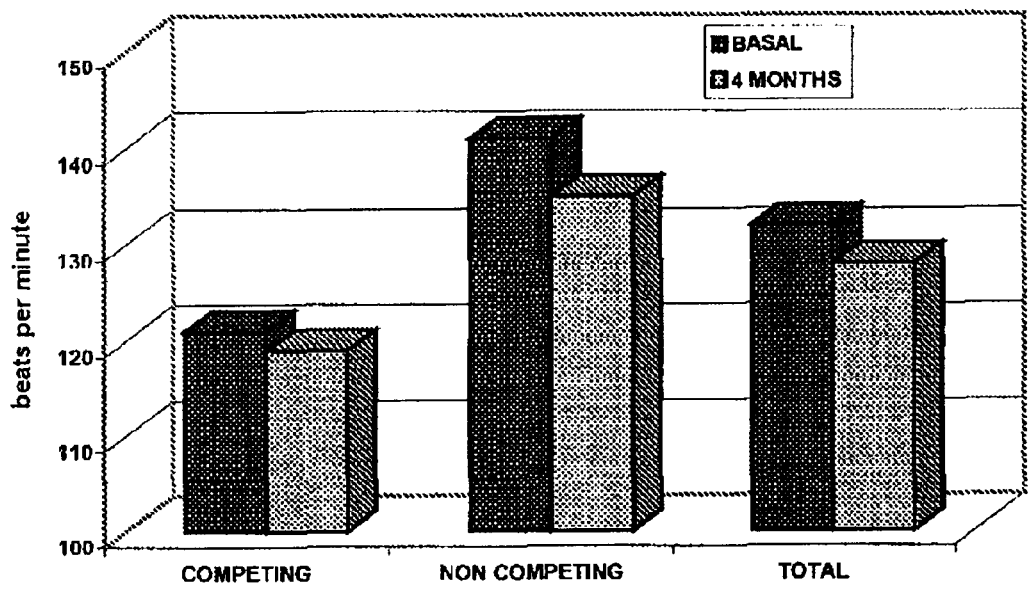
FIG. 27 is a graphic representing the cardiac frequency during the consumption of 2000 ml/min $O_2$ in the ventilatory threshold for competing, non-competing and all cyclists at basal level and after 4 months taking DHA.
Figure 28:
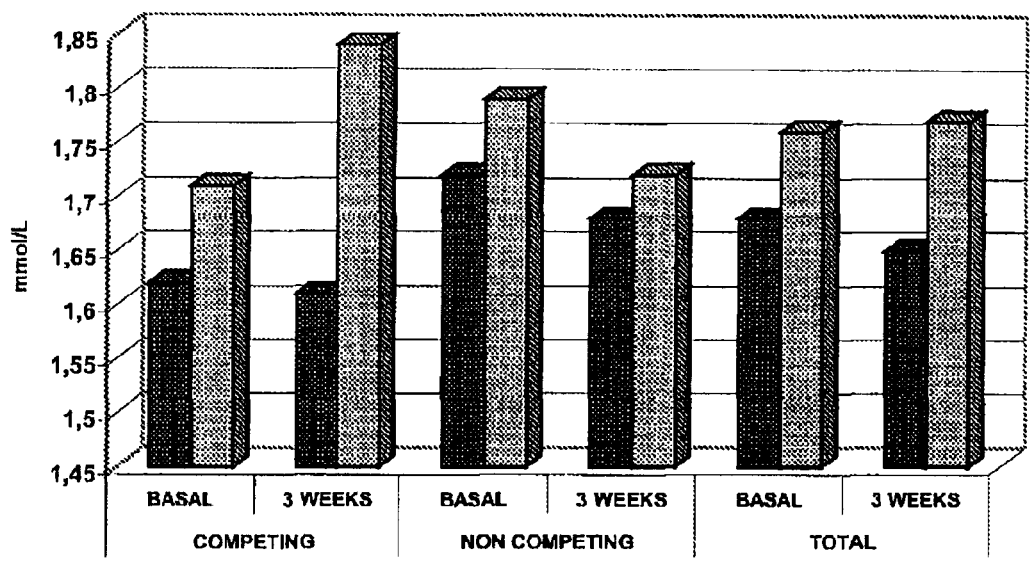
FIG. 28 is a graphic representing the plasma total antioxidant capacity for competing, non-competing and all sportsmen at basal level and after 3 weeks taking DHA. In each case, there is shown the antioxidant capacity before (left bar) and the antioxidant capacity after (right bar) the effort trial.
Figure 29:
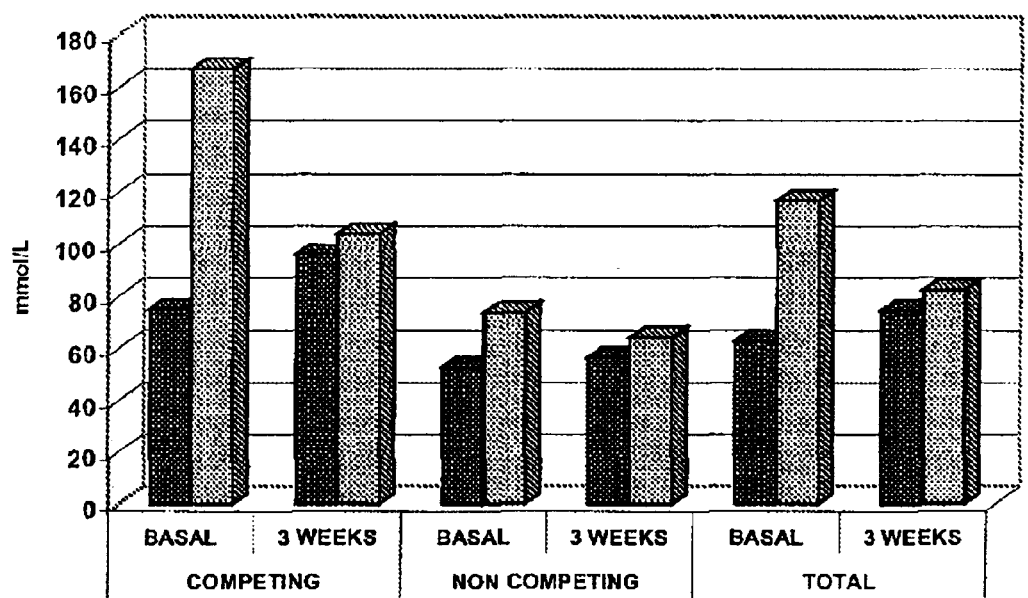
FIG. 29 is a graphic representing the oxidative damage to plasmatic lipids according to MDA concentration for competing, non-competing and all sportsmen at basal level and after 3 weeks taking DHA. In each case, there is shown the oxidative damage before (left bar) and the oxidative damage after (right bar) the effort trial.
Figure 30:
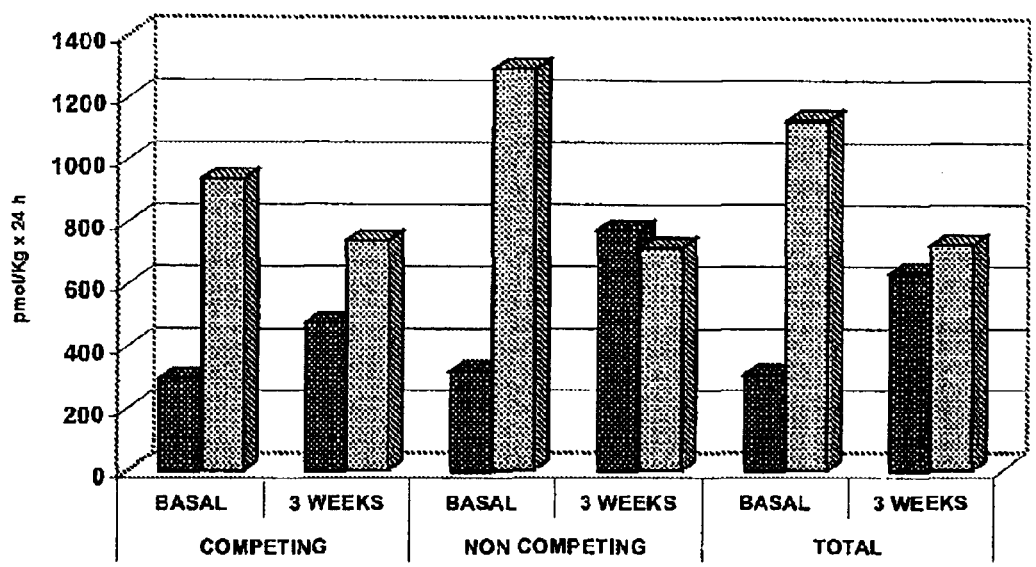
FIG. 30 is a graphic representing the oxidative damage to DNA using the oxidative stress biomarker 8-oxodG for competing, non-competing and all sportsmen at basal level and after 3 weeks taking DHA. In each case, there is shown the oxidative damage before (left bar) and the oxidative damage after (right bar) the effort trial.
Figure 31:
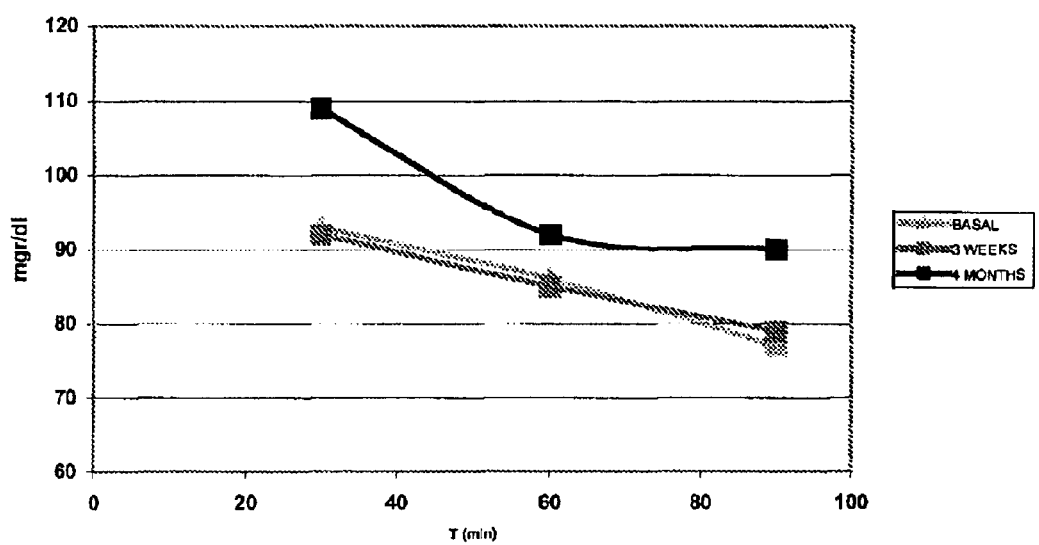
FIG. 31 is a graphic representing the glycemia in competing sportsmen during a physical effort who did not take DHA or did it for 3 weeks or 4 months.
Figure 32:
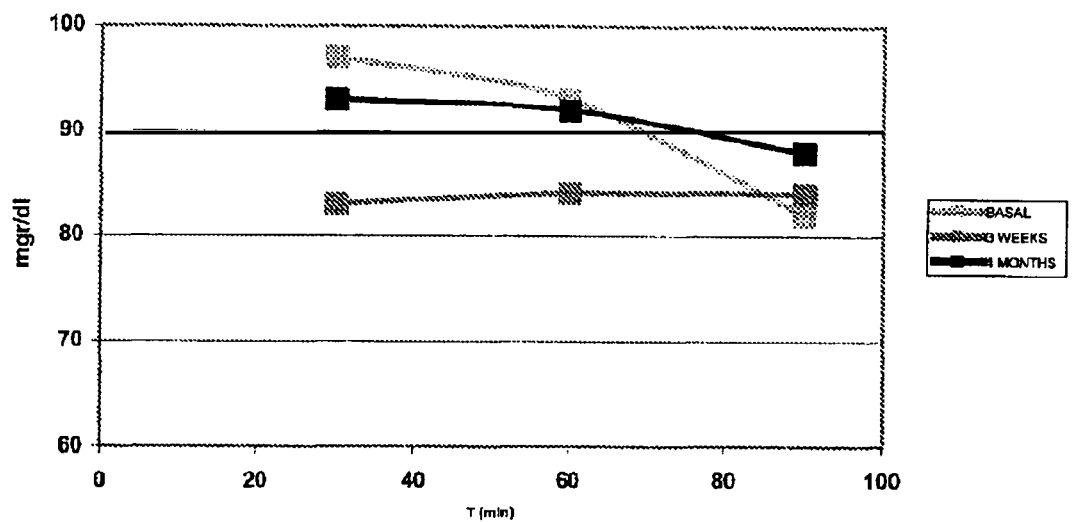
FIG. 32 is a graphic representing the glycemia in non-competing sportsmen during a physical effort who did not take DHA or did it for 3 weeks or 4 months.
Figure 33:
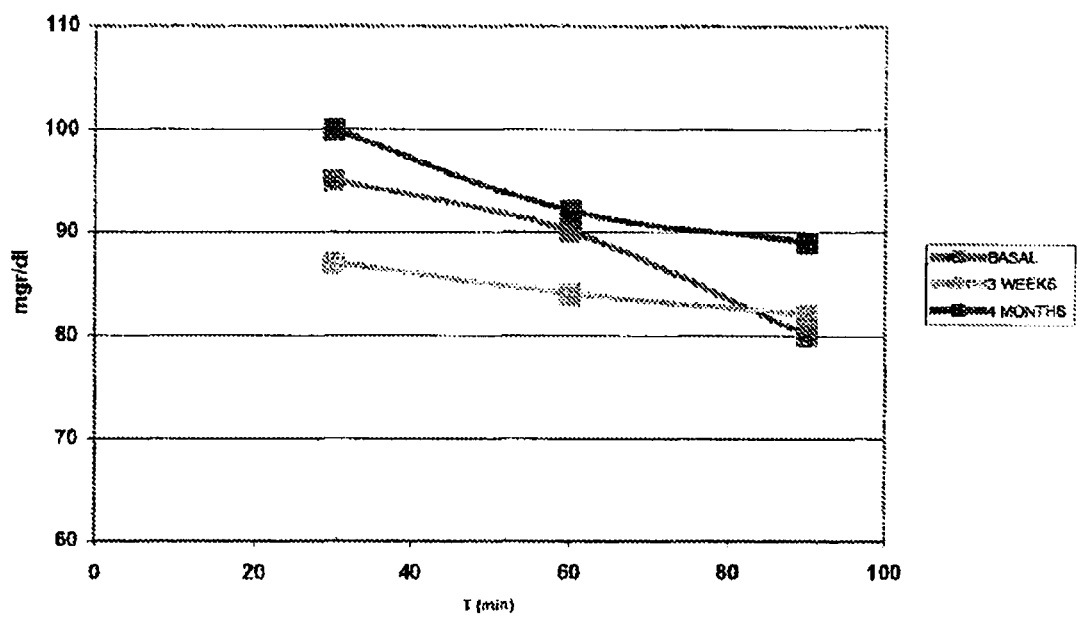
FIG. 33 is a graphic representing the glycemia in competing and non-competing sportsmen during a physical effort who did not take DHA or did it for 3 weeks or 4 months.

Changes in the average length of telomeres in human fibroblasts cultured under oxidative stress conditions with or without incorporated DHA were analysed by flow-FISH (FIG. 23). A linear regression was used to analyse the relation between the length of telomeres and the pass number of cellular populations. For all the analysed cultures, the slopes in the regressions can be understood directly as the telomere shortening index. In human fibroblasts, the treatment with AAPH, which induces an excess of intracellular free radicals, accelerate noticeably the telomere shortening index. On the other hand, the incorporation of DHA at a concentration of 0.5 μM, which has been proved to increase the cell antioxidant defence, reduces said index by 50% in respect to its value without DHA. Furthermore, the incorporation of DHA is capable of reducing the telomere shortening index, even in respect to the normal control of fibroblasts.

The invention claimed is:

1. A method of treating cellular oxidative damage comprising administering a foodstuff comprising docosahexaenoic acid (DHA), eicosapentaenoic acid (EPA), or DHA-derived EPA to a subject affected by cellular oxidative damage associated with a neurodegenerative pathology, wherein said DHA, EPA, or DHA-derived EPA is enzymatically incorporated into a glyceride,
a portion of said DHA, EPA, or DHA-derived EPA being incorporated into an sn-2 position of the glyceride.

2. The method according to claim 1, wherein the cellular oxidative damage comprises production of a reactive oxygen species.

3. The method according to claim 2, wherein the reactive oxygen species comprises a superoxide anion.

4. The method according to claim 1, wherein the cellular oxidative damage comprises a shortening of DNA telomeres.

5. The method according to claim 1, wherein the cellular oxidative damage comprises a premature cellular senescence.

6. The method according to claim 1 wherein said neurodegenerative pathology is selected from multiple sclerosis, Alzheimer's disease, Parkinson's disease, amiotrophic lateral sclerosis, or muscular dystrophy.

7. A method for treating cellular oxidative damage comprising administering an effective amount of docosahexaenoic acid (DHA), eicosapentaenoic acid (EPA), or DHA-derived EPA to a subject affected by cellular oxidative damage associated with a neurodegenerative pathology, wherein said DHA, EPA, or DHA-derived EPA is enzymatically incorporated into a glyceride,
a portion of said DHA, EPA, or DHA-derived EPA being incorporated into an sn-2 position of the glyceride.

8. The method of claim 7, wherein the cellular oxidative damage comprises production of a reactive oxygen species.

9. The method of claim 8, wherein the reactive oxygen species comprises a superoxide anion.

10. The method of claim 7, wherein the cellular oxidative damage comprises a shortening of DNA telomeres.

11. The method of claim 7, wherein the cellular oxidative damage comprises a premature cellular senescence.

12. The method of claim 7, wherein said neurodegenerative pathology is selected from multiple sclerosis, Alzheimer's disease, Parkinson's disease, amiotrophic lateral sclerosis, or muscular dystrophy.

13. The method of claim 7, wherein said docosahexaenoic acid (DHA), eicosapentaenoic acid (EPA), or DHA-derived EPA is administered in dairy products.

14. The method of claim 7, wherein said docosahexaenoic acid (DHA), eicosapentaenoic acid (EPA), or DHA-derived EPA is administered through a beverage before, during or after physical exercise; an energy-giving bar; ergogenical bars; solids and preparations for provisioning; dietetic supplement and polivitaminic preparation; ergogenical aids; or textiles with nanocapsules for skin absorption.

15. The method of claim 14, wherein said dietetic supplement and polyvitaminic preparation are in the form of capsules, tablets, pills, or lyophilised form.

16. The method of claim 7, wherein said docosahexaenoic acid (DHA), eicosapentaenoic acid (EPA), or DHA-derived EPA is administered in a cosmetic application.

17. The method of claim 7, wherein said glyceride is a triglyceride.

18. The method of claim 17, wherein between 40 and 100% by weight of fatty acids in the triglyceride are the DHA, EPA, or DHA-derived EPA.

19. The method of claim 17, wherein between 66 and 100% by weight of fatty acids in the triglyceride are the DHA, EPA, or DHA-derived EPA.

20. The method of claim 7, wherein $C_1$—$C_8$ short chain fatty acids are incorporated in an sn-1 position, an sn-3 position, or both of the glyceride.

21. The method of claim 7, wherein phosphoric acid is incorporated in an sn-1 position, an sn-3 position, or both of the glyceride.

22. The method of claim 1, wherein said glyceride is a triglyceride.

23. The method of claim 22, wherein between 40 and 100% by weight of fatty acids in the triglyceride are the DHA, EPA, or DHA-derived EPA.

24. The method of claim 22, wherein between 66 and 100% by weight of fatty acids in the triglyceride are the DHA, EPA, or DHA-derived EPA.

25. The method of claim 1, wherein $C_1$-$C_8$ short chain fatty acids are incorporated in an sn-1 position, an sn-3 position, or both of the glyceride.

26. The method of claim 1, wherein phosphoric acid is incorporated in an sn-1 position, an sn-3 position, or both of the glyceride.

* * * * *